(12) United States Patent
Eteminan et al.

(10) Patent No.: US 11,020,003 B2
(45) Date of Patent: Jun. 1, 2021

(54) PATIENT MONITORING AND COMMUNICATION SYSTEM

(71) Applicant: FONECLAY, INC., Rancho Santa Fe, CA (US)

(72) Inventors: Isaac Eshagh Eteminan, Rancho Santa Fe, CA (US); James William Bishop, Jr., Reno, NV (US); Oscar Rangel, San Marcos, CA (US)

( * ) Notice: Subject to any disclaimer, the term of this patent is extended or adjusted under 35 U.S.C. 154(b) by 0 days.

(21) Appl. No.: 16/182,509

(22) Filed: Nov. 6, 2018

(65) Prior Publication Data
US 2019/0133445 A1    May 9, 2019

Related U.S. Application Data

(60) Provisional application No. 62/582,872, filed on Nov. 7, 2017.

(51) Int. Cl.
*A61B 5/00*     (2006.01)
*A61B 5/021*    (2006.01)
(Continued)

(52) U.S. Cl.
CPC ............ *A61B 5/0024* (2013.01); *A61B 5/002* (2013.01); *A61B 5/0022* (2013.01); *A61B 5/021* (2013.01);
(Continued)

(58) Field of Classification Search
CPC ... A61B 5/0024; A61B 5/0402; A61B 5/4205; A61B 5/747; A61B 5/0826; A61B 5/6814; A61B 5/1116; A61B 5/1495; A61B 5/1112; A61B 5/0476; A61B 5/0022; A61B 5/002; A61B 5/681; A61B 5/021;
(Continued)

(56) References Cited

U.S. PATENT DOCUMENTS

2005/0146431 A1*   7/2005   Hastings ............ G08B 21/0294
                                                                 340/539.12
2012/0078661 A1*   3/2012   Sheldon ................. G06Q 50/24
                                                                 705/3
(Continued)

*Primary Examiner* — An T Nguyen
(74) *Attorney, Agent, or Firm* — Kilpatrick Townsend & Stockton LLP

(57) ABSTRACT

A patient monitoring and communication system uses a patient sensor package and a care operations service suite able to retrieve and analyze data from the patient sensor package. The patient sensor package comprises a number of sensors measuring body functions and indicators relevant to health. A number of communication interfaces with both wired and wireless connectivity is utilized. A number of user interfaces with audio/visual and haptic connectivity and an application suite supports automatic collection of sensor information by the care operations service suite. A care operations message server interacts with the patient sensor packages and provides message services corresponding to their configuration, connection, location, sensor, and presentation managers. Web portal services are provided to administrator, caregiver, patient, and family member users; and a management server interacts with system managers and providing log, data backup, software update, file transfer, command-line, and graphical control management services.

21 Claims, 16 Drawing Sheets

(51) Int. Cl.
- *G16H 80/00* (2018.01)
- *A61B 5/08* (2006.01)
- *A61B 5/11* (2006.01)
- *A61B 5/1495* (2006.01)
- *A61B 5/318* (2021.01)
- *A61B 5/369* (2021.01)
- *G16H 10/60* (2018.01)
- *A61B 5/0205* (2006.01)
- *A61B 5/145* (2006.01)
- *A61B 5/087* (2006.01)

(52) U.S. Cl.
CPC .......... *A61B 5/0826* (2013.01); *A61B 5/1112* (2013.01); *A61B 5/1116* (2013.01); *A61B 5/1495* (2013.01); *A61B 5/318* (2021.01); *A61B 5/369* (2021.01); *A61B 5/4205* (2013.01); *A61B 5/681* (2013.01); *A61B 5/6814* (2013.01); *A61B 5/747* (2013.01); *G16H 80/00* (2018.01); *A61B 5/02055* (2013.01); *A61B 5/087* (2013.01); *A61B 5/14532* (2013.01); *A61B 5/14542* (2013.01); *A61B 5/6805* (2013.01); *A61B 5/6843* (2013.01); *A61B 2560/0214* (2013.01); *A61B 2562/028* (2013.01); *A61B 2562/0219* (2013.01); *A61B 2562/0247* (2013.01); *A61B 2562/08* (2013.01); *G16H 10/60* (2018.01)

(58) Field of Classification Search
CPC ........ A61B 2560/0214; A61B 5/14542; A61B 5/087; A61B 5/14532; A61B 2562/08; A61B 5/6843; A61B 2562/0247; A61B 5/6805; A61B 2562/028; A61B 2562/0219; A61B 5/02055; G16H 80/00; G16H 10/60; G16H 40/40; G16H 40/63; G16H 40/67

See application file for complete search history.

(56) References Cited

U.S. PATENT DOCUMENTS

| | | | | |
|---|---|---|---|---|
| 2013/0060167 | A1* | 3/2013 | Dracup | G16H 50/20 600/595 |
| 2014/0085082 | A1* | 3/2014 | Lyon | A61B 5/0205 340/539.12 |
| 2014/0142963 | A1* | 5/2014 | Hill | G16H 10/60 705/2 |
| 2014/0276552 | A1* | 9/2014 | Nguyen, Jr. | A61M 5/14248 604/503 |
| 2015/0097701 | A1* | 4/2015 | Al-Ali | G06F 21/84 340/870.07 |
| 2015/0332007 | A1* | 11/2015 | Rosebraugh | G06Q 30/0205 705/2 |
| 2016/0287166 | A1* | 10/2016 | Tran | A61B 5/165 |
| 2018/0004909 | A1* | 1/2018 | Cronin | G16H 20/17 |
| 2018/0325385 | A1* | 11/2018 | Deterding | G16H 50/20 |
| 2019/0052710 | A1* | 2/2019 | Heinz | H04L 67/16 |
| 2019/0133445 | A1* | 5/2019 | Eteminan | A61B 5/6814 |

* cited by examiner

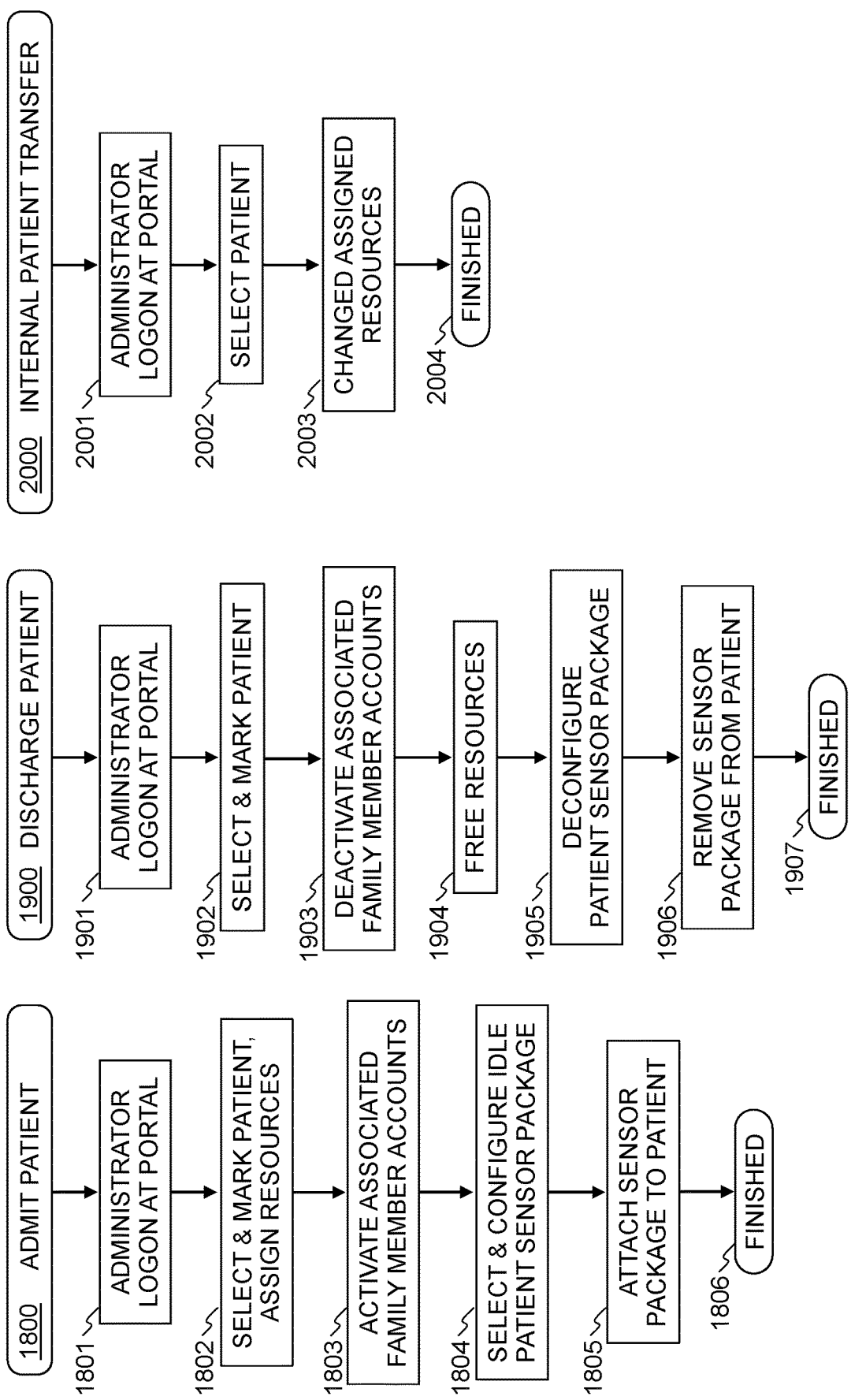

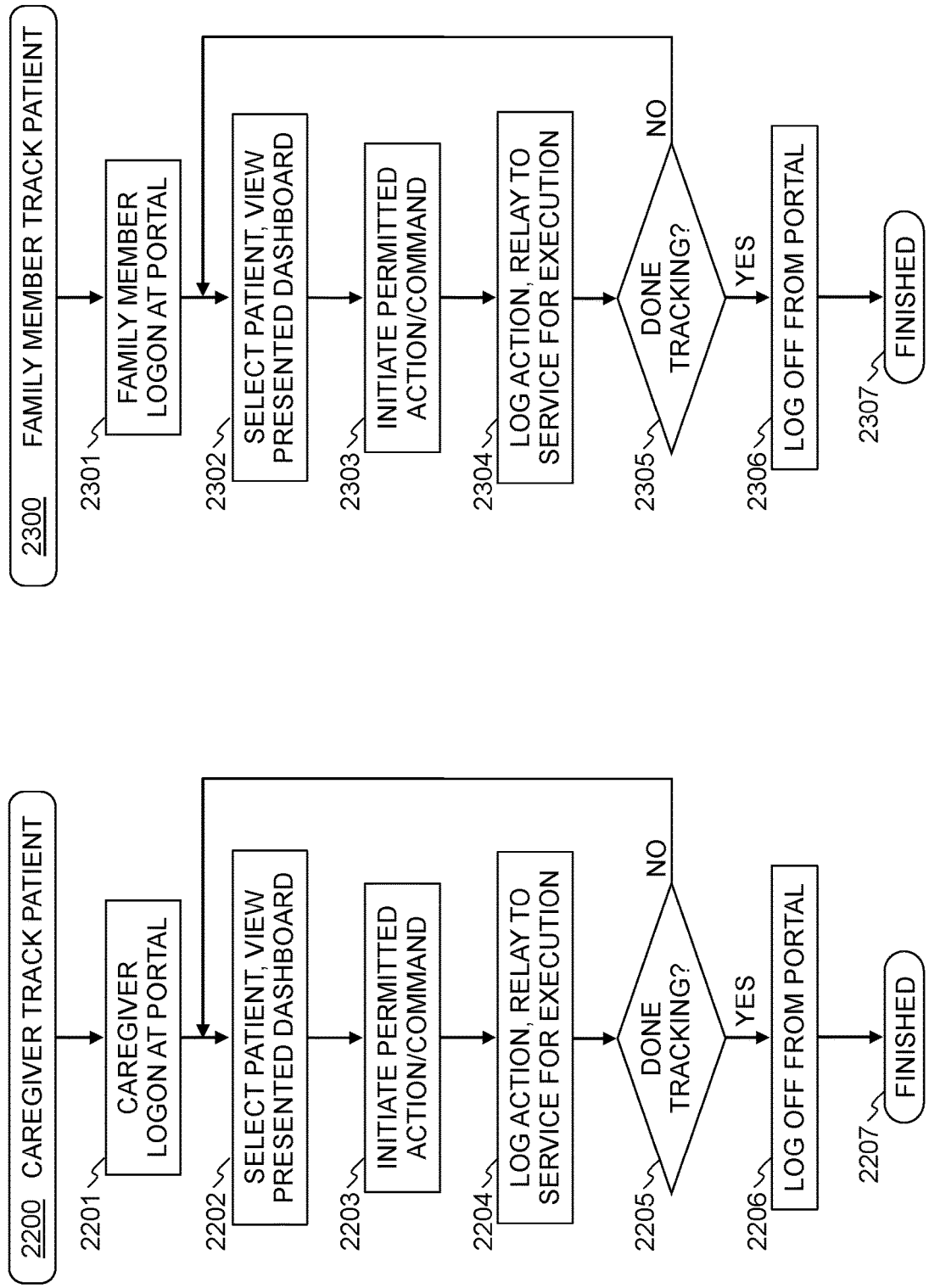

PATIENT MONITORING AND COMMUNICATION SYSTEM

CROSS-REFERENCE TO RELATED APPLICATIONS

This application claims the benefit and priority of U.S. Provisional Patent Application Ser. No. 62/582,872, filed on Nov. 7, 2017, the contents of which is hereby incorporated by reference in its entirety.

FIELD

This invention relates to patient monitoring and service. More particularly, the invention relates to a patient monitoring and communication system with cloud-connected caregiver workstations.

BACKGROUND

Healthcare applications of information and communication technology are growing rapidly, with many new developments appearing constantly in such areas as electronic medical records, personal fitness trackers, doctor-patient communication, diagnostic sensors, and many more. Too many product and service offerings exist to enumerate even a fraction of them here. In fact, new offerings are emerging so rapidly that it is quite impossible to know about everything that exists. In such an environment, all that can be done is to describe a new solution on its own terms without attempting to compare it to others. What can be stated, however, is that integrated systems tying all of these elements together such that information from wearable sensors monitoring stationary and mobile patients is connected in a meaningful fashion to mobile caregivers and records systems are rare, and systems that do this in multiple environments both controlled and uncontrolled are more so.

Therefore, there exists a need for a patient monitoring and communication system that integrates an inexpensive body-worn sensor package with secure monitoring capability connected via multiple telecommunication options to a care operations service suite; that interprets the reported sensor data and provides appropriate corresponding information to caregivers; that provides a path for real-time audio, text, video, and multi-mode conversation between patient and caregiver; that protects the patient privacy of sensor data, interpretations, and real-time conversations over all telecommunication paths, in all presentation modes, and in all storage locations; that incorporates multiple form factors of body-worn sensor packages in order to support adaptation to patients with varying abilities and conditions; that incorporates care operations service suite deployments both in a common facility shared by multiple care providers, and in a care provider's own facility; and that operates successfully across multiple patient care venues including controlled environments such as hospitals and nursing homes, uncontrolled environments such as patient homes and the world at large (for example, during a nursing home resident's occasional outings with family members), and in hybrid environments such as outpatient clinics and hospice centers.

SUMMARY

The following presents a simplified summary in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

In one aspect of the disclosure, a patient monitoring and communication system is provided, comprising: a patient sensor package; and a care operations service suite able to retrieve and analyze data from the patient sensor package.

In another aspect of the disclosure, the above system further comprises an administrator workstation and a caregiver workstation; and/or wherein the workstations and care operations service suite allow an administrator user to enroll, admit, transfer, and discharge patients; and/or wherein the workstations and care operations service suite allow a caregiver user to track patient information, monitor a patient via a patient sensor package, and communicate with a patient via a patient sensor package; and/or further comprises a family member personal computing device; and/or wherein the workstations, personal computing device, and care operations service suite allow a family member user to track patient information, monitor a patient via a patient sensor package, and communicate with a caregiver; and/or wherein the patient sensor package comprises: an embedded computer with memory and processing capability; a number of sensors measuring body functions and indicators relevant to health; a number of communication interfaces with both wired and wireless connectivity; a number of user interfaces with audio/visual and haptic connectivity; and an application suite supporting automatic collection of sensor information by the care operations service suite; and/or wherein the patient sensor package application suite further supports audio, audio/visual, and text communication between a patient and a caregiver; and/or wherein the patient sensor package takes the form of a wristwatch; and/or wherein the patient sensor package takes the form of a chestband; and/or wherein the patient sensor package takes the form of a headband; and/or wherein the patient sensor package takes the form of a choker necklace; and/or wherein the patient sensor package takes the form of a sash or vest; and/or wherein the patient sensor package takes the form of a hat; and/or wherein the patient sensor package takes the form of a belt; and/or wherein the patient sensor package takes the form of an armband; and/or wherein the patient sensor package takes the form of a sock or glove; and/or wherein the patient sensor package takes the form of a pendant; and/or wherein the care operations service suite comprises: a care operations message server interacting with patient sensor packages and providing message services corresponding to their configuration, connection, location, sensor, and presentation managers; a care operations web server interacting with users and providing portal web services to administrator, caregiver, patient, and family member users; and a management server interacting with system managers and providing log, data backup, software update, file transfer, command-line, and graphical control management services; and/or wherein the care operations service suite further comprises a communication and monitoring connections gateway; and/or wherein the care operations service suite further comprises an external information database gateway; and/or wherein the care operations service suite further comprises an autonomous data analysis and application support platform that provides notification and action initiation, diagnostic event correlation, and diagnostic trend detection capabilities; and/or wherein the care operations service suite is implemented using shared computing elements in a virtual private cloud provided by a HIPAA-compliant public cloud service, and accessed via the Internet; and/or wherein the care operations service suite is implemented using dedicated computing elements located in a caregiver's facility, and accessed via a local area network; and/or wherein the care operations service suite is implemented using shared computing elements in a private cloud located in a caregiver's corporate data center, and accessed via a virtual private network carried over the Internet.

In yet another aspect of the disclosure, a patient sensor package in a patient monitoring and communication system is provided, comprising: an embedded computer with memory and processing capability; a number of sensors measuring body functions and indicators relevant to health; a number of communication interfaces with both wired and wireless connectivity; a number of user interfaces with audio/visual and haptic connectivity; and an application suite supporting automatic collection of sensor information by the care operations service suite.

In yet another aspect of the disclosure, the above system is provided, wherein the application suite further supports audio, audio/visual, and text communication between a patient and a caregiver; and/or the patient sensor package is in the form of a wristwatch; and/or is in the form of a chestband; and/or is in the form of a headband; and/or, is in the form of a choker necklace; and/or is in the form of a sash or vest; and/or is in the form of a hat; and/or in the form of a belt; and/or in the form of an armband; and/or in the form of a sock or glove; and/or in the form of a pendant.

In yet another aspect of the disclosure, a care operations service suite in a patient monitoring and communication system is provided, comprising: a care operations message server interacting with patient sensor packages and providing message services corresponding to their configuration, connection, location, sensor, and presentation managers; a care operations web server interacting with users and providing portal web services to administrator, caregiver, patient, and family member users; and a management server interacting with system managers and providing log, data backup, software update, file transfer, command-line, and graphical control management services.

In yet another aspect of the disclosure, the above system is provided, further comprising a communication and monitoring connections gateway; and/or further comprises an external information database gateway; and/or further comprises an autonomous data analysis and application support platform that provides notification and action initiation, diagnostic event correlation, and diagnostic trend detection capabilities; and/or is implemented using shared computing elements in a virtual private cloud provided by a HIPAA-compliant public cloud service, and accessed via the Internet; and/or is implemented using dedicated computing elements located in a caregiver's facility, and accessed via a local area network; and/or is implemented using shared computing elements in a private cloud located in a caregiver's corporate data center, and accessed via a virtual private network carried over the Internet.

In yet another aspect of the disclosure, a method of operating a patient monitoring and communication system is provided, the method comprising: enrolling and admitting a patient, and assigning caregivers to the patient; selecting a patient sensor package, assigning it to the patient, configuring it to connect via a network to a care operations service suite, and attaching it to the patient's body; automatically configuring the patient sensor package to send sensor data and other information to the care operations service suite according to care facility policies and practices, and according to caregiver settings; storing data received from the patient sensor package in a database at the care operations service suite; and presenting sensor data to a caregiver.

In yet another aspect of the disclosure, the above method is provided, further comprising: transferring a patient from one care facility to another; automatically reconfiguring the patient sensor package to connect via a different network at the new facility to a different care operations service suite associated with the new facility; automatically assigning caregivers associated with the new care facility to the patient; and automatically reconfiguring the patient sensor package to reflect different facility policies and preferences as well as different caregiver settings; and/or further comprises: discharging the patient, and collecting and deconfiguring the patient sensor package; and/or further comprises: facilitating audio, audio/visual, and text communication between the patient and a caregiver; and/or further comprises: enrolling a family member permitted to participate in the patient's care; presenting sensor data to the family member; and facilitating audio, audio/visual, and text communication between the family member and a caregiver, as well as between the patient and the family member.

BRIEF DESCRIPTION OF THE DRAWINGS

FIGS. 14-23 illustrates a group of processes distributed across multiple elements in a patient monitoring and communication system according to an exemplary embodiment of the invention.

DETAILED DESCRIPTION

The following detailed description describes currently contemplated modes of carrying out exemplary embodiments of the invention. The description is not to be taken in a limiting sense, but is made merely for the purpose of illustrating the general principles of some embodiments. Accordingly, the embodiments described below are understood to illustrate only some possible examples of the invention's operation, configuration, etc. Other examples will be evident to one of ordinary skill in the art and is understood to be within the spirit and scope of this disclosure.

For example, various features are described below that can each be used independently of one another or in combination with other features. Broadly, some embodiments generally provide patient monitoring and communications systems and algorithms.

A first exemplary embodiment of the disclosure provides a patient monitoring and communication system comprising one or more patient sensor packages, one or more caregiver workstations, and a care operations service suite that may be deployed in a cloud platform as a shared resource used by multiple enterprises or in an appliance platform dedicated to a single enterprise.

A second exemplary embodiment of the disclosure provides a patient sensor package incorporating multiple medical and non-medical sensors in a wearable form, and incorporating behaviors that integrate it as part of a patient monitoring and communication system.

A third exemplary embodiment of the disclosure provides a care operations service suite that may be deployed in a cloud platform as a shared resource used by multiple enterprises or in an appliance platform dedicated to a single enterprise, and incorporating behaviors that integrate it as part of a patient monitoring and communication system.

A fourth exemplary embodiment of the disclosure provides a method of operating a patient monitoring and communication system.

The preceding is intended to serve as a brief introduction to various features of some exemplary embodiments of the invention. Other embodiments may be implemented in other specific forms within the scope of this disclosure.

I. Hardware Architecture

Figure 1:
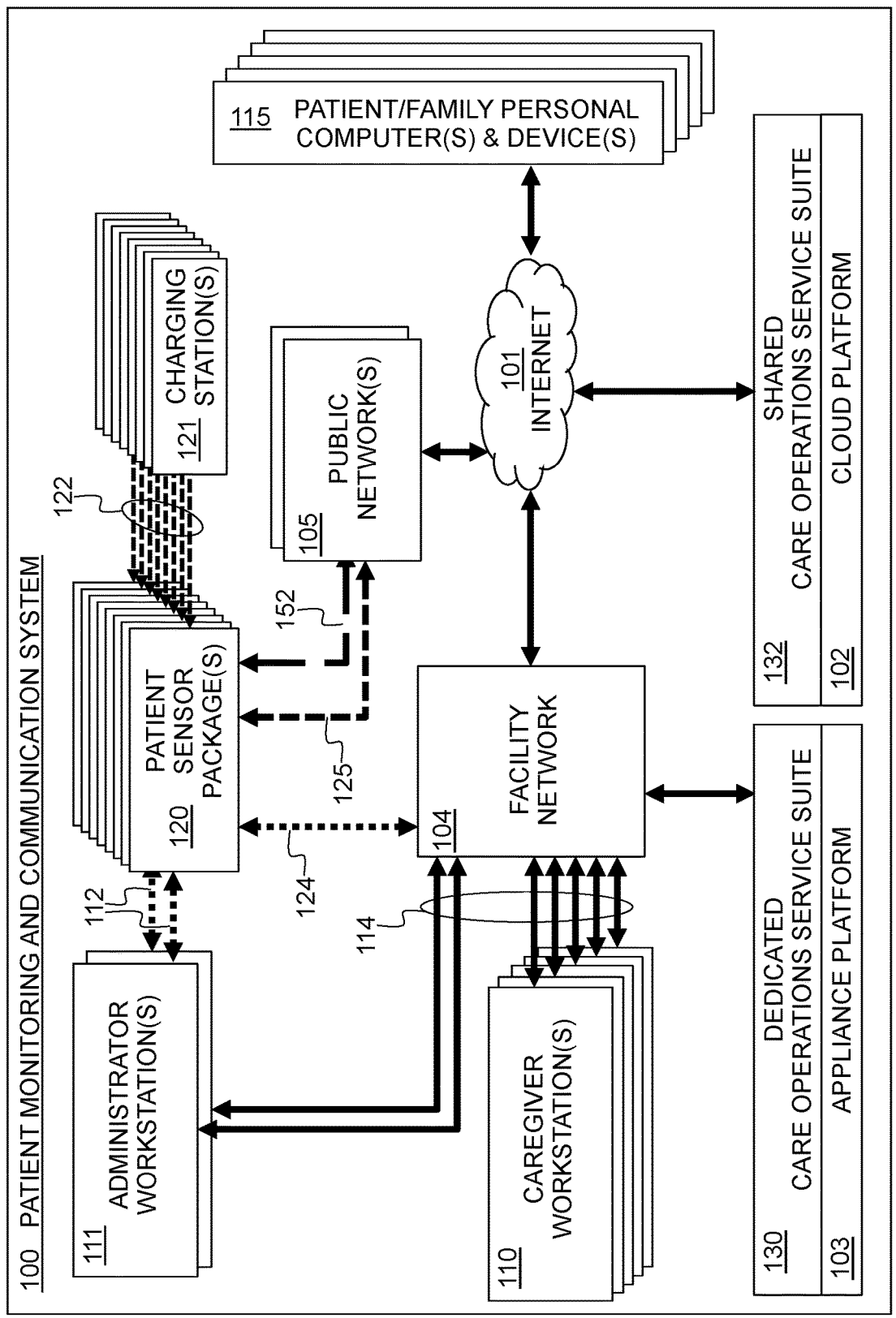
FIG. 1 illustrates a schematic block diagram of a patient monitoring and communication system according to an exemplary embodiment of the invention.

FIG. 1 illustrates a schematic block diagram of a patient monitoring and communication system 100 according to an exemplary embodiment.

Patient sensor package 120 may be a wearable device such as a wristband/watch, neckband, headband, chest band, waistband, anklet, hat, etc. One or more may be included in system 100 as deployed for a facility. Patient sensor package 120 may provide a user interface to patient and/or caregivers for multiple functions. Patient sensor package 120 may include sensors such as heartrate, blood pressure, temperature, motion, and location, and may provide a continuous flow of readings to a care operations service suite 130 or 132 for interpretation and action by caregivers. Patient sensor package 120 may also provide communication capabilities so patient and caregiver can talk, text, video call, etc. The patient sensor package may be battery operated to enable patient mobility and caregiver convenience; the battery (not shown) may be charged via a charging station 121 with one of several possible interfaces 122 customized according to facility requirements. Wired interfaces may include USB, barrel plug, dedicated contact pins, etc. Wireless options may include magnetic/inductive (Qi) and optical/infrared (Wi-Charge).

Patient sensor package 120 may connect to facility network 104 when in-facility, using a Wifi Network Interface 124 (and/or other appropriate interfaces). The patient sensor package 120 may also be configured to connect via various protocols to various public networks 105 and thence back into the facility network 104 via the Internet 101, when the patient is outside the facility (possible scenarios include a nursing home resident visiting family or an outside doctor, a post-surgery patient being monitored during at-home recovery, and numerous others). Public network protocols may include Wifi via interface 125, cellular data such as LTE, UMTS, etc. via interface 152, depending on availability.

Caregiver workstations 110 may present information about each patient from each patient sensor package 120. A caregiver workstation 110 may provide capabilities to communicate with patients via audio, video, and text; send reminders to patients; and monitor a patient's environment via audio and/or video. Caregivers may logon to caregiver workstations 110 using assigned credentials, so that each workstation 110 may present information for and allow communication with only those patients assigned to the logged-on caregiver.

Administrator workstations 111 may be a privileged type of caregiver workstation 110. In addition to capabilities cited above for caregiver workstations 110, Administrator workstation 111 capabilities may include assigning patients to caregivers; registering and deregistering patients; assigning patient sensor packages 120 to patients; and configuring patient sensor packages. A new patient sensor package may be connected directly to an administrator workstation 111 in order to receive its initial configuration such as Wi-Fi parameters and other facility settings; direct connection via interface 112 may be accomplished using wired (e.g., USB) or wireless (e.g., Bluetooth) interfaces depending on facility requirements.

Caregiver and administrator workstations 110/111 may connect to the facility network 104 via interfaces 114 using standard LAN (e.g., Ethernet) and/or WLAN (e.g., Wi-Fi) technologies, depending on facility requirements.

Patient/family personal computers and devices 115 may participate in the care system 100 via information portals provided by care operations service suite 130 or 132, using dedicated logons provisioned upon patient registration, to access patient status information and, if allowed, specific medical information.

For each facility the care operations service suite (COSS) may provide a fixed point for collecting, processing, and storing sensor data and other information from patient sensor packages 120; authenticating caregiver and administrator workstation 110/111 logons; presenting patient information to authorized caregivers; and facilitating communication (audio, text, video, notifications) between caregivers, patients, and others.

Two kinds of COSS may be provided; the type used depends on facility requirements; both may also be deployed in a primary/backup relationship if appropriate. Dedicated COSS 130 may be deployed in the facility or in a private network to which the facility network is connected. The dedicated COSS may provide COSS functionality implemented in an appliance platform 103. A dedicated COSS 130 is only available to the associated facility, with corresponding data privacy and related security advantages.

Shared COSS 132 may be deployed in a Cloud Platform 102 and may serve all facilities that do not have a dedicated COSS 130. The shared COSS 132 may also provide several levels of backup service to those facilities with a dedicated COSS 130, such as data archive, cold/warm/hot redundancy, or peak load processing, depending on facility requirements. Cloud platform 102 may be required to provide HIPAA-compliant security and privacy capabilities as well, since COSS functionality may include medical information regulated by HIPAA.

Figure 2:
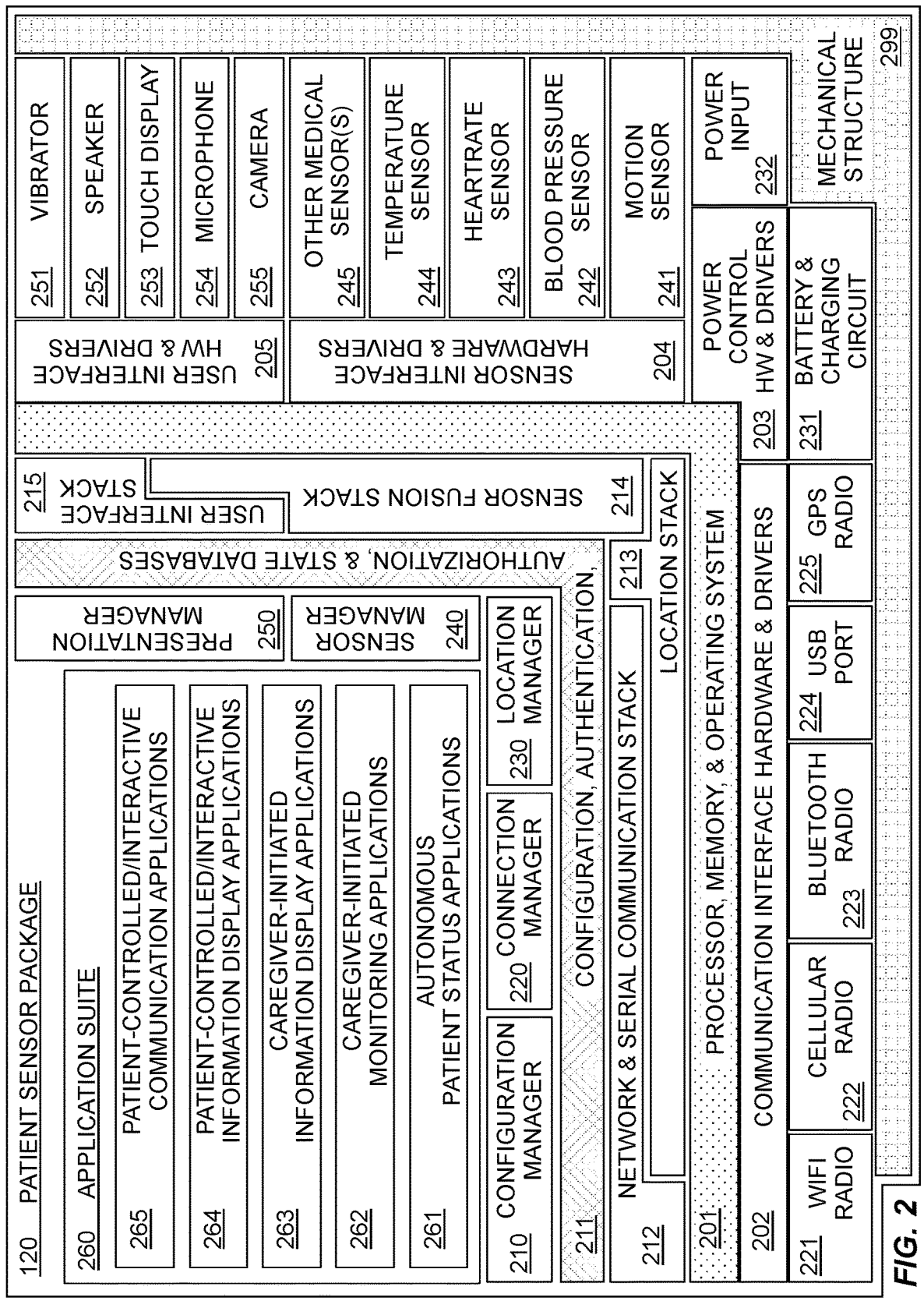
FIG. 2 illustrates a schematic block diagram for a patient sensor package in a patient monitoring and communication system according to an exemplary embodiment of the invention.

FIG. 2 illustrates a schematic block diagram of a patient sensor package 120 in a patient monitoring and communication system according to an exemplary embodiment.

Patient sensor package 120 may include the sensors, processors, communication capabilities, user interaction capabilities, application functions, and structural properties of a wearable unit participating in patient monitoring and communication system 100. Each instance of the patient sensor package 120 described in reference to system 100 may include the various elements included in FIG. 2.

The sensors, interfaces, and logic of the patient sensor package 120 may be embedded in a mechanical structure 299, which may provide physical containment, one or more body-attachment elements, and the mechanical aspects of the interfaces (openings, connectors, etc.). Variations on mechanical structure may primarily be due to specializations for the body-attachment features, and to some degree also may be due to related specializations for the physical containment. Exemplary physical forms may be numerous, and include several described herein.

One exemplary form may be a wristwatch or wristband, in which sensors and user interface (UI) elements are compact and tightly integrated. In such a form, a display screen may be very small and presentation capabilities may be limited to only a few elements at a time, while battery capacity may be limited to a few hours of operation between charges due to the small size.

Another exemplary form may be a chest band or waistband/belt, which may feature more sensors and longer battery life due to a larger physical format. Additional sensors may also be provided based on being worn across the chest or abdomen, particularly including ultrasound, heart sensors such as ECG/EKG, or even actuators such as an external defibrillator. In this form some user interface elements, especially a display, may be omitted or tuned for caregiver viewing instead of patient viewing due to angle and position.

Still another exemplary form may be a headband, again featuring potentially more sensors and longer battery life due to the larger format (compared with wristband), and again possibly featuring additional sensors based on being worn across the skull—in this case various brain sensors such as EEG or mini-fMRI. Here as well, certain user interface elements such as a display screen may be omitted or tuned for caregiver use due to inability of a patient to see a screen worn on the head.

Yet another exemplary form may be a sash or vestment, worn either around the back of the neck and draped down the front of the body, or across one shoulder and crossing both the front and back of the body to join at the waist or hip. This form may potentially feature even more sensors and longer battery life due to its larger format and less burdensome body position, and additional sensors may be provided based on being worn across chest, neck, and back; again ECG/EKG, ultrasound, and external defibrillator may be included, as well as respiratory sensors or a high-sensitivity body-directed microphone to act as a remote stethoscope.

Another exemplary form may be a choker-style necklace/neckband, with size and sensor/battery capacity somewhere between that of the wristwatch and the headband. Appropriate additional sensors may include adaptations for the blood pressure and heartrate sensors to measure swallowing and breathing, or to detect apnea. Many other forms are possible as well, including but not limited to hats, socks, armbands, pendants; essentially anything that fits any specific body area.

Once inside the physical containment provided by mechanical structure 299, the hub of the sensor package 120 may be an embedded computer surrounded by sensors and interfaces. Processor, memory, and operating system 201 may form the core of this embedded computer, and are typical of the type with one or multiple processing cores, dynamic and static memory, and so forth. At least four classes of peripheral may be included, each with their corresponding hardware and operating system kernel driver software—communication interface hardware and drivers 202, power control hardware and drivers 203, sensor interface hardware and drivers 204, and user interface hardware and drivers 205.

Communication interface hardware and drivers 202 may provide ways for patient sensor package 120 to attach to external networks and participate in system 100. Multiple types of communication path may be appropriate, of which five are shown here. Wi-Fi Radio 221 may support attachment to a wireless LAN using one or more variants of the 802.11 standard, such as may be provided by facility network 104 or certain public network(s) 105 using interfaces 124 or 125.

Cellular radio 222 may support attachment to a wide-area wireless network using one or more of the many public wireless carrier standards, such as LTE, HSPA, UMTS, EDGE, GSM, and so forth, that may be provided by certain public network(s) 105 using interface 152.

Bluetooth radio 223 may support short-range wireless attachment, using preferably the most recent but alternatively any version of the Bluetooth standard, to a nearby computer such as administrator workstation 111, thereby providing an interface 112 path for secure configuration of and data extraction from patient sensor package 120.

USB port 224 may be available to support a wired attachment to administrator workstation 111, providing the same capabilities as cited for Bluetooth radio 223.

GPS radio 225 may support reception of geolocation signals from Global Positioning System and similar satellites and calculation therefrom of an absolute position of the patient sensor package 120 device. Additional communication features may also be provided, such as a Zigbee radio, an Ethernet port, or any other of the multitude of standard and proprietary protocols.

Power control hardware and drivers 203 may provide ways for patient sensor package 120 to receive, store, and control the expenditure of energy to support processing, sensing, and communication functions.

Battery and charging circuit 231 may manage storage and charging, and may be sized according to a variety of use cases. For example, a hospital use case may allow for nearly continuous charging from a wireless energy source, so the battery may be relatively small. As another example, an outpatient use case may allow for charging only once per day or even once per week, so that battery may be relatively large.

Power input 232 may provide a path (e.g., interface 122) for external energy to be acquired by the battery and charging circuit 231 (e.g., from charging station 121). The specific form of power input 232 may vary according to use case. For example, an optical charging feature such as Wi-Charge may be applied in a hospital-like setting case where the corresponding charging stations 121 can be deployed ubiquitously. Magnetic charging solutions such as Qi may be applied in a setting where patient sensor package 120 can be routinely removed from the patient and set on the corresponding charging mat. Wired charging solutions may also be applied where appropriate, such as in settings where a patient or caregiver can connect a charger to device 120 for an extended rest period. In such a case, power input 232 may share connector hardware with USB port 224, and a variant of charging station 121 may even be embedded in an administrator workstation 111.

Sensor interface hardware and drivers 204 may provide input paths for readings that become medical information, and may include analog inputs for digitizing and measuring continuous voltages and intermittent or regular voltage pulses; digital inputs for directly receiving encoded numeric values; and digital or analog outputs for enabling non-continuous sensor devices or controlling actuators that assist in creating an appropriate environment for certain measurements.

The driver portion of sensor interface hardware and drivers 204 may be responsible for interpreting the raw data read from each sensor and converting it, possibly in conjunction with calibration data, into the appropriate units of measurement.

Motion sensor 241 may include one or more accelerometers to provide indications of relative movement in any direction. The motion sensor may be implemented using a number of technologies, including optical gyroscope and MEMS.

Blood pressure sensor 242 may measures the patient's blood pressure, a common medical indicator; this sensor may include an inflatable cuff as part of the mechanical structure 299, along with a motorized inflator, or it may incorporate recently-developed optical techniques.

Heartrate sensor 243, which may be implemented as a subset of blood pressure sensor 242, may measure the patient's pulse or heartrate. The heartrate sensor 243 may include optical, electromechanical, piezoelectric, or other types of sensors.

Temperature sensor 244 may measure the patient's body temperature, another essential medical indicator. Any of the common optical, infrared, or thermoelectric techniques may be included.

Finally, patient sensor package 120 may include additional sensors beyond the aforementioned, either in future versions as new sensors are developed, or in alternate implementations that satisfy specialized requirements for particular use cases, settings, or form factors. Such variations are represented in as other medical sensor(s) 245. Examples may include a glucose monitor, a pulse oximeter, an electrocardiogram, an electroencephalogram, a brainwave sensor, a nerve conduction sensor, a breath analyzer, and others too numerous to list or not yet invented.

User interface hardware and drivers 205 may provide input and output paths for interactions with the person wearing patient sensor package 120. The hardware may be similar to corresponding features in other devices used for communication, such as smartphones, smartwatches, and tablet computers.

Vibrator 251 may provide haptic feedback for notifications and simulated keypresses. Speaker 252 may generate audio/sound. Touch display 253 may present visual information and provide finger-driven or stylus-driven input signals. Camera 255 may provide still and motion video input, and may be adapted or generalized to any light-sensing capability. Camera 255 may be a conventional visible-light imager, or it may be a multi-spectral imager capable of capturing light beyond the visible spectrum.

Where the various hardware and driver modules include the outward-facing or physical functions of patient sensor package 120 and can be considered as peripherals of the computation resources in processor, memory, and operating system 201, opposite them in FIG. 2 are the various software functional modules that constitute the programming for those computation resources and build up to perform the inventive behaviors of patient sensor package 120. The modules may be further categorized as stacks, databases, managers, and applications.

Stacks may provide utility functions that implement higher-layer protocols, paradigms, and/or abstractions atop the physical capabilities of hardware and drivers, such as arranging bits on a communication path into IP packets, or arranging pixels on a display into polygons. Databases may provide storage of and shared access to configuration and state information. Managers may structure the utilization of database and stack capabilities according to the intent of the inventive behavior; they enable, interpret, and disable resources, both autonomously as appropriate for fundamental use-case scenarios and under control of applications for situational scenarios within a fundamental use-case. Finally, applications may implement the interactive and configured inventive behaviors of the patient sensor package 120.

Network and serial communication stack 212 may provide TCP/IP, AMQP, HTTP, TLS, and other upper-layer protocols for interoperability with external entities over the various communication interfaces.

Location stack 213 may use information from the various communication interfaces, including in particular GPS radio 225 but also taking advantage of ranging and connectivity capabilities available from the others for contextual indications, as well as from various sensors, including in particular motion sensor 241 but again also taking advantage of background and contextual indications available from some of the others, to determine and track where the patient sensor package 120—and therefore the patient wearing it—is located. Location stack 213 may also provide functions that integrate this position with location-related information such as maps; functions that interpret additional context data from sensor fusion Stack 214, such as background audio from microphone 254 or background video from camera 255, and incorporate that data into position, velocity, and direction information; and functions that pass raw and/or filtered radio signal measurements from the various radio interfaces to other modules, including in particular to sensor fusion stack 214, for use in combining multiple data sources.

Sensor fusion stack 214 may collect data from sensors, user inputs, and potentially radio receivers to track and store basic indications, as well as to provide compound indications such as respiration rate from a combination of heartrate, motion, and audio data, or moods such as anxiety, anger, serenity, etc. from a combination of temperature, heartrate, blood pressure, vocal stress analysis, and facial analysis.

User interface stack 215, as mentioned above, may provide utilities such as converting abstract polygons, text, and colors into display pixel combinations, routing audio and video streams, and interpreting touch indications as button presses and touch gestures. The user interface stack may also provide functions for interpreting motion sensor data provided through sensor fusion stack 214 as movement gestures. User interface stack 215 may also provide functions for translating text to speech and speech to text, and for translating text or speech from one or more natural languages to one or more other natural languages. In what may be the ultimate combination of these capabilities, user interface stack 215 may also provide functions for interpreting the patient's movements and gestures as recorded by motion sensor 241, or a caregiver's movements and gestures as recorded by camera 255, as symbols in one or more of the standard sign languages used by people with hearing impairments, and translating those symbols to text or speech.

Configuration, authentication, authorization, and state databases 211 may provide a central data repository within the patient sensor package 120, in which all the other functional modules and applications store information and through which they exchange information with one another. Configuration information may include persistent knowledge such as patient identity and medical records linkage, caregiver linkage(s), communication network parameters, and sensor calibrations. State information may include transient records such as sensor readings, battery charge level, position, display content, and active communication paths. In between, authentication and authorization information may provide the security-oriented basis of trust for establishing communication paths both at the level of attaching the device to the network and at the level of sharing information between patient and caregivers.

As previously noted, managers may structure the utilization of database and stack capabilities according to the intent of the inventive behavior. The managers may enable, interpret, and disable resources, both autonomously as appropriate for fundamental use-case scenarios and under control of applications for situational scenarios within a fundamental use-case. To those ends, connection manager 220 performs the job of noticing which communication interfaces 202 are available, and setting up end to end connections over them using the various protocols in stack 212 as well as the configuration and authentication information in databases 211. In order to operate communication and battery resources in a mutually optimal manner, connection manager 220 may also use battery state of charge information recorded in databases 211 to balance availability of communication with consumption of energy. Applications and other managers in turn utilize the communication paths maintained by connection manager 220 to perform their functions.

Configuration manager 210 may operate in conjunction with the corresponding functional module in administrator workstation 111 to maintain the content of configuration, authentication, and authorization data in databases 211. Configuration changes are generally pushed into patient sensor package 120 from administrator workstation 111 upon command from an administrative user. Some changes may only be made while directly attached to administrator workstation 111 via USB port 224 or Bluetooth radio 223, such as the identity of the patient wearing sensor package 120, mutual authentication certificates for patient sensor package 120 and care operations service suite 130 or 132, and parameters for attachment to facility network 104 via Wi-Fi radio 221. Other changes, such as caregiver authorizations or sensor and location reporting frequencies, may be made while attached via any available communication path.

Location manager 230 may monitor position and movement information in database 211 (state data) as provided by location stack 213, and periodically relay the information to authorized recipients identified in database 211 (authorization data). Authorized recipients may include an authenticated care operations service suite 130 or 132, an authenticated public network 105 to which patient sensor package 120 is attached via cellular radio 222, a 911 call application that could in turn relay location information to an emergency service provider, and other applications such as geo-fencing or fall detection that detect when a patient's location and/or movement become anomalous and in turn initiate corresponding patient, caregiver, and/or external alerts.

Sensor manager 240 may monitor sensor readings that appear in database 211 (state data) as provided by sensor fusion stack 214, and periodically relay the readings to authorized recipients identified in database 211 (authorization data). Authorized recipients may include an authenticated care operations service suite 130 or 132, an information display application that presents important medical measurements to the patient via presentation manager 250, or a vitals monitoring application that detects when a patient's medical measurements become anomalous and in turn initiates patient and/or caregiver alerts.

Presentation manager 250 may control the structure and content of what is output to the user interface, and the routing of what is input from the user interface.

Application suite 260 may provide a number of top-level functions that enable patient and caregiver access to information generated by the aforementioned components of patient sensor package 120. Applications in suite 260 may be considered in groups as described in subsequent paragraphs. Note that groupings like this are used for descriptive convenience to draw upon certain commonalities among the applications in each group, and the particular grouping used here is not necessarily the only grouping possible, nor does it necessarily constrain the arrangement of information or controls in the implementation.

Autonomous patient status applications 261 may be automatically initiated and operate continuously to detect health-related anomalies in the sensor information flow. For example, a geo-fence application may be deployed to track the patient's location and check that the patient remains within a certain area, such as the buildings and grounds of a memory-care facility, and alert one or more caregivers when the patient crosses an area boundary. A fall detector application may track the patient's fine movement via motion sensor 241 to detect dangerous situations such as falling or not moving for too long, alerting caregivers of such events and if appropriate also initiating an emergency phone call (e.g., 911, 112, 999, or other number depending on jurisdiction). Similarly, a vital signs application may track individual sensor readings and composite indications from sensor fusion stack 214 to detect off-nominal or out-of-range medical conditions, sleepwalking, seizures, or other undesirable behaviors and events, again alerting caregivers as needed; dangerous conditions, such as might indicate heart failure or death, may trigger an emergency call as well. Additional autonomous applications may be conceived and implemented in this architecture as it evolves.

Caregiver-initiated monitoring applications 262 may be started remotely as needed by a caregiver, upon passing authentication and authorization as indicated in the corresponding sections of databases 211. If authorized, such applications may operate without explicit interactive approval from the patient, allowing a caregiver to observe conditions or surroundings unobtrusively, as when the patient may be asleep or otherwise unable to respond. For example, an audio and/or video monitor application may enable microphone 254 to hear the patient's breathing, or enable camera 255 to see the patient's surroundings or body position. Also, considering that the vital signs application described in the previous paragraph may only track primary medical indicators such as temperature, pulse, and blood pressure, and sensor fusion stack 214 may produce additional complex indicators such as mood or stress level, corresponding applications in this category may be implemented so caregivers are able to observe these additional indicators as needed.

Caregiver-initiated information display applications 263 may be started remotely as needed by a caregiver, upon passing authentication and authorization as indicated in the corresponding sections of databases 211. If authorized, such applications may operate without explicit interactive approval from the patient, allowing a caregiver to control user interface outputs. For example, an alerting application may use one or more of video, audio, and vibration to present a reminder, instruction, or notification to the patient, including but not limited to instructing the patient to wake up or return to the facility, reminding the patient to exercise or take a medication, or notifying the patient of an upcoming appointment. A biofeedback support application may ensure selected medical indicators are presented continuously on the display 253, regardless of whatever else is being shown.

Patient-controlled/interactive information display applications 264 may be started at the patient's request using touch indications or speech commands, and operate interactively under the patient's control via the various user interface capabilities. For example, a self-alerting application may allow the patient to set alarms that use one or more of video, audio, and vibration to present a self-defined reminder, instruction, or notification at a certain time or under one or more specified sensor conditions. A medical information display application may ensure selected medical indicators are presented continuously on the display 253, regardless of whatever else is being shown. A location and navigation application may display the patient's position relative to a map, or provide navigation guidance to a particular destination either within the facility or in the world at large as appropriate.

Patient-controlled/interactive communication applications 265 may support person-to-person audio, video, or text communication between patient and caregiver, and if authorized between patient and other parties. For example, the patient may initiate a call or send a message, or a caregiver may initiate a call or send a message, in either case with routing and notification of the destination party facilitated by connection manager 220 and corresponding capabilities in care operations service suite 130 or 132. In the case of a call or message initiated by a caregiver or outside party, the patient has control of whether to accept the communication. The patient may set a do-not-disturb status to reject calls and messages automatically as well. If authorized, or if the patient is away from the facility such as in the case of a nursing home resident visiting family or the case of a post-surgery patient recuperating at home, an emergency call application may support placing a call to the appropriate emergency service (e.g., 911, 112, 999, etc.).

The example applications described for each category are not meant to provide an exhaustive list. Additional applications may be conceived within each category, as well as in any number of other categories not described herein.

Figure 3:
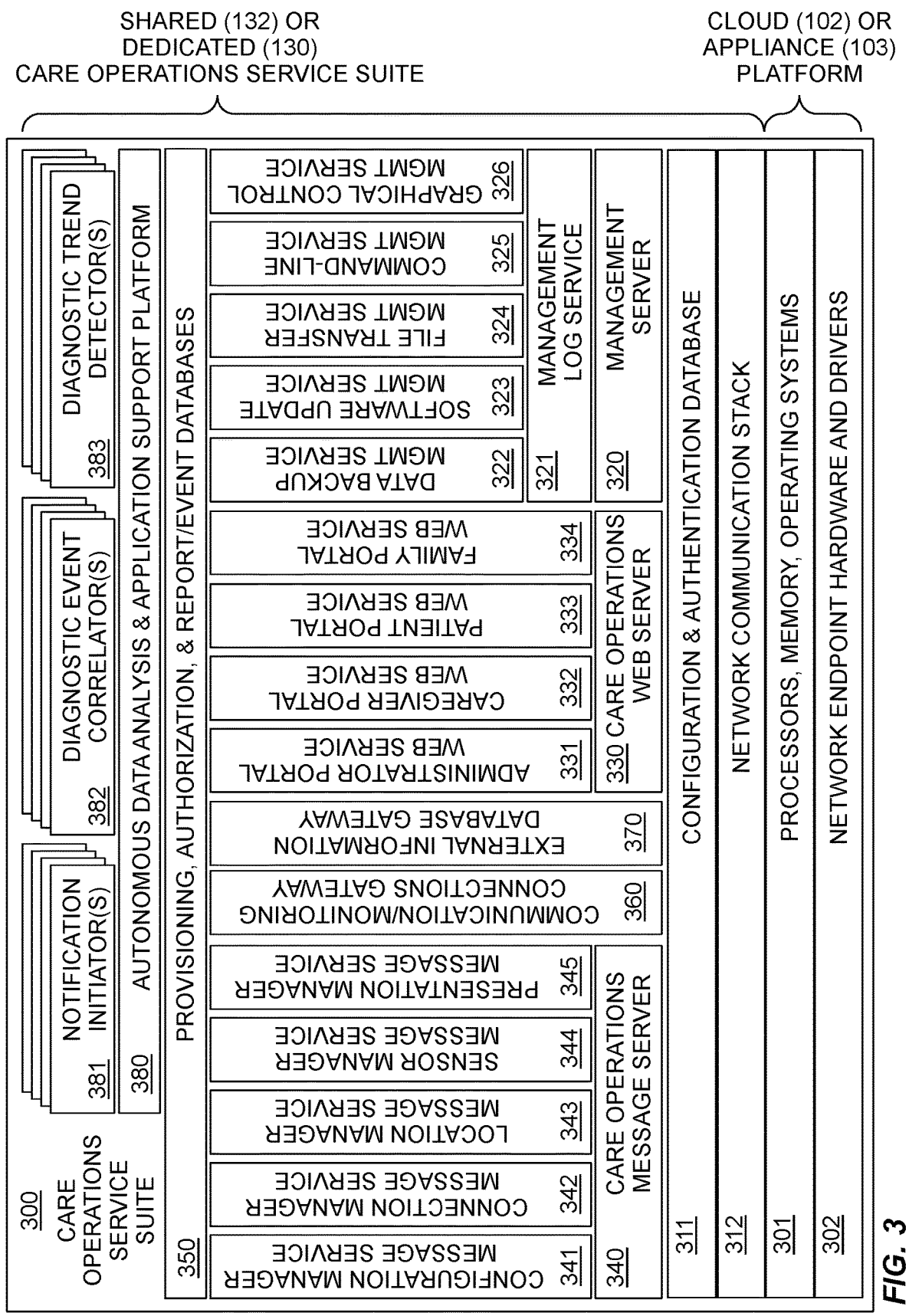
FIG. 3 illustrates a schematic block diagram for a care operations service suite in a patient monitoring and communication system according to an exemplary embodiment of the invention.

FIG. 3 illustrates a schematic block diagram for a care operations service suite 300 in a patient monitoring and communication system 100 according to an exemplary embodiment. These functions may be deployed for a particular customer in either or both of a dedicated care operations service suite 130 located within the customer's facility, or a shared care operations service suite 132, as described above. These options are generalized as Care operations service suite 300, where the functional modules indicated by the long upper bracket map to the shared 132 or dedicated 130 care operations service suite variations from system 100, and the functional modules indicated by the short lower bracket map deployment to the cloud 102 or appliance 103 platform variations from system 100.

Platform elements may include processors, memory, and operating systems 301, as well as network endpoint hardware and drivers 302. These may be implemented as either a cloud platform 102 or an appliance platform 103. In either case, any particular deployment may include multiple physical or virtual computing machines according to capacity, availability, and security requirements of the upper-layer functions, as is usual for such platforms. Numerous subsystem functions may then be constructed atop the platform functions.

Network communication stack 312 may be similar to network and serial communication stack 212, and may provide TCP/IP, AMQP, HTTP, TLS, and other upper-layer protocols for interoperability with external entities via the network endpoint elements of the platform. External entities in this case may include not only the multiple patient sensor packages 120, administrator workstations 111, and caregiver workstations 110 of patient monitoring and communication system 100, but also entities external to that system such as electronic health record databases and other medical information systems operated within or on behalf of the same facility operating system 100, as well as personal computers and mobile devices operated by patients and their family members to access information resident in care operations service suite 300.

Configuration and authentication database 311 may provide a data repository specifically for information about care operations service suite 300. Configuration information may include, but is not limited to, such persistent knowledge as how it relates to the network in which it resides, how the various function modules are deployed across potentially multiple physical and/or virtual computing machines, and licensed capacity. Authentication information may provide the security-oriented basis of trust for establishing communication paths both at the level of attaching the services hosted in care operations service suite 300 to other services elsewhere in the network, and at the level of authenticating access to its management functions.

II. Services

Beyond those foundations, the functions of care operations service suite 300 naturally fall into a few major groups. The first of these includes the management functions, which provide ways to configure and control the care operations service suite 300. Management server 320 may form the basis of the management function group, providing a network interface and an operating environment for the various management services. Management server 320 may include such components as a web server, a secure shell interface, a file transfer protocol server, and related capabilities typically used in the management of information technology systems.

Management log service 321 may ensure that every access of management server 320 from a controlling user (ordinarily called an administrator in the information technology industry, but named differently here so as not to be confused with the care operations administrator role), whether successfully authenticated or rejected, is recorded. Actions commanded by authenticated controlling users, as well as automatic actions performed by the various management services may also be recorded or logged. The placement of management log service 321 parallel to management server 320 indicates that service 321 acts as a support function for all the management services, enabling the responsibility of the service to log everything that happens.

The remaining management services may provide the usual functionality one finds in network element management. Certain key features are identified explicitly here, but others may be included as well.

Data backup management service 322 may provide ways to routinely capturing consistent snapshots of all data in care operations service suite 300, including the contents of configuration and authentication database 311 as well as the contents of provisioning, authorization, and report/event databases 350, and securely conveying each snapshot to an external repository.

Software update management service 323 may provide ways for securely receiving, authenticating, validating, and activating new software loads and configuration data for care operations service suite 300.

File transfer management service 324 may provide ways for securely sending and receiving general data files, and may be used both independently and as a support function for data backup management service 322 as well as software update management service 323.

Command-line management service 325 may receive typed user commands that may change state or display information in a line-by-line terminal mode, while graphical control management service 326 may provide buttons and select menu items that may change state or display information on a graphical interface mode and are able to be selected by a user.

The next major group of functions may provide access for various types of user in the care community served by care operations service suite 300. At the heart of this group is care operations web server 330, which may support highly secure information presentation for multiple users and user roles. Support for each user role may be encapsulated within a corresponding service built onto the care operations web server, partitioned from the others to prevent inappropriate information crossover.

Administrator portal web service 331 may support the care administrator role, and may be accessed from administrator workstations 111. The care administrator may primarily view and manipulate provisioning information—the identities of and relationships between people who are active in care operations—and generally does not view or manipulate medical information. The care administrator may enroll caregivers and patients (as well as their family members, where appropriate), assign relationships between caregivers and patients, initialize patient sensor packages 120, and assign specific patient sensor packages 120 to specific enrolled patients. Administrator portal web service 331 may presents forms and screens and commands to facilitate these activities.

Caregiver portal web service 332 may support the caregiver role, and may be accessed from caregiver workstations 110. The caregiver may primarily view and manipulate medical information, and may also view provisioning information where necessary to ensure correct patient and family member identity. Caregivers may view both current and historical medical information including sensor readings and alerts, initiate presentation of specific medical information to a patient on the corresponding patient sensor package 120, initiate communication with or monitoring of a patient via the corresponding patient sensor package 120, and record notes and observations associated with care of a patient.

A caregiver may also be able to, depending on configuration of caregiver portal web service 332 in conjunction with external information database gateway 370 and corresponding external capabilities, access/present/manipulate a patient's data in the facility's electronic health record and related systems. Caregiver portal web service 332 may present forms and screens and commands to facilitate these activities.

Patient portal web service 333 may support the patient role, and may be accessed from patient/family personal computers and devices 115, as well as from one or more shared workstations provided within the facility (not shown, these may be considered a kind of patient/family personal computer or device 115). The patient may generally receive a constrained view of medical information, where the constraints are set on a per-facility, per-caregiver, or per-patient basis depending on the information sharing policies of the facility. The patient may also be able to edit some provisioning information (such as insurance numbers or family member authorizations), again depending on facility policy as configured via the management services. Patient portal web Service 333 may present forms and screens and commands to facilitate these activities.

Family Portal Web Service 334 may support the family member role, and may be accessed from patient/family personal computers and devices 115, as well as from one or more shared workstations provided within the facility. A family member may generally receive a constrained view of patient status and possibly medical information, where the constraints are set on a per-facility, per-caregiver, or per-patient basis depending on the information sharing policies of the facility. Family portal web service 334 may present forms and screens and commands to facilitate these activities.

The next major group of functions may provide access to the care operations service suite 300 for those patient sensor packages 120 that are deployed within or otherwise associated with the facility. At the heart of this group may be care operations message server 340, which may support highly secure information transfer, via a high-performance protocol such as AMQP, between the manager functions in multiple patient sensor packages 120 and corresponding services in care operations service suite 300.

Configuration manager message service 341 may communicate with configuration manager 210 in each deployed patient sensor package 120 to provide the sensor package settings and update the sensor package firmware, as well as to read that data back when needed to verify them.

Connection manager message service 342 may communicate with the connection manager 220 in each deployed patient sensor package 120 to support establishment and teardown of audio, text, and video sessions, providing for those capabilities the signaling path that governs the stream connections made via communication/monitoring connections gateway 360.

Location manager message service 343 may communicate with location manager 230 in each deployed patient sensor package 120 to collect the location data stream of the sensor package, as well as any location-related events or alerts created autonomously within the patient sensor package.

Sensor manager message service 344 may communicate with sensor manager 240 in each deployed patient sensor package 120 to collect each package's sensor data stream, its aggregate or fused sensor data, and any sensor-related events or alerts created autonomously within the patient sensor package.

Presentation manager message service 345 may communicate with presentation manager 250 in each deployed patient sensor package 120 to display information to a patient at the request of a caregiver, and to reflect to a caregiver what is being displayed to a patient.

Provisioning, authorization, and report/event databases 350 may provide operational data storage for care operations service suite 300. Provisioning data may include the set of records representing each patient, patient sensor package 120, caregiver, caregiver workstation 110, administrator, administrator workstation 111, and/or patient family member known within the system. Provisioning data for each represented participant may include, but is not limited to, identifying information, logon credentials within care operations service suite 300, linkages/credentials for external communication networks accessed through communication/monitoring connections gateway 360, and linkages/credentials for EHR and other systems accessed through the external information database gateway 370.

Authorization data may include the set of records representing relationships between patients and patient sensor packages 120, between patients and caregivers, and between patients and patient family members, as well as the information each can see about the other. Report/event data may record everything coming into care operations service suite 300 from all patient sensor packages 120 via care operations message server 340, including sensor readings, communication requests, and monitoring streams, as well as from care participants via care operations web server 330, including data requests, communication requests, and monitoring commands. Report/event data may also include the state of each web service, message service, communication connection, monitoring connection, and external data access activity. Services, gateways, and other modules of care operations service suite 300 may communicate with one another through these databases 350 to cooperate in providing care capabilities, while ensuring that all data in the system is recorded so it can be available for medical histories or external analysis as needed.

As previously mentioned, communication/monitoring connections gateway 360 may provide ways to relay communication streams such as audio, video, and text between a patient wearing a sensor package 120 and a caregiver logged into caregiver portal web service 332, or family member logged into family portal web service 334, or any other combination of these care participants. The gateway 360 may also provide multi-party call capabilities, for example allowing a patient and family member in different rooms to confer with a caregiver at the same time. Gateway 360 may also connect streams externally, such as for an audio call between a patient and someone in the public telephone network via an external internet-phone system, if authorized.

Also, as previously mentioned, external information database gateway 370 may provide ways to access external data such as an electronic health records system that may be serving the same facility as care operations service suite 300, in order to incorporate that external data into caregiver and patient information streams. Gateway 370 may also provide the reverse data flow, wherein patient data from care operations service suite 300 may be made available to an external database, again including but not limited to an EHR system. Gateway 370 may also provide a data path to/from one or more other care operations service suites 300 via its/their respective external information database gateway(s) 370, thereby enabling sharing of information between facilities for such purposes as, for example, referring patients to specialists, transferring patients to facilities with higher or lower levels of care, or moving patients between affiliated facilities in conjunction with a family relocation or corporate load balancing.

At the highest level of functionality in care operations service suite 300 are a variety of autonomous actors that respond to service events and analyze data, initiating notifications and other actions as appropriate. Providing a context for these actors is autonomous data analysis and application support framework 380. Framework 380 may include utility functions for examining swaths of data from databases 350, for monitoring streams of events from the various services and gateways, and for passing new data and events back into the databases, services, and gateways as appropriate. Each actor working in the context of framework 380 may be specifically programmed to examine a particular kind of data or event, and may create new data or events as a result.

Three classes of autonomous actor are depicted, and additional classes may be devised in the context of framework 380 as well. Notification initiators 381 may be actors that recognize certain data as calling for a notification to be sent, either to a patient, to a caregiver, or to another care participant or external entity. Examples include, but are not limited to, requests for timed reminders as set by a patient or caregiver using their respective portals 332 or 333, termination of timed monitoring or communication connections, and alerts due to data flagged as anomalous by a diagnostic actor.

Diagnostic event correlators 382 may be actors that examine the event data flow for a particular patient, group of patients, or caregiver, and identify anomalies based on the order or frequency of events as they occur. Such actors may be programmed to find medical anomalies such as undetected diseases in a patient's sensor data stream, for example, or to notice a pattern indicating abuse of privileges or even patient mistreatment by a caregiver. If a condition is found, a correlator 382 may set a flag in database 350 for an initiator 381 to notify a care participant, or for a service to present at a portal.

Diagnostic trend detectors 383 may be actors that examine sensor data flow and notice anomalies based on the direction a particular reading or set of readings is heading for a particular patient. In this way, the detectors may provide capabilities within care operations service suite 300 that are similar to the capabilities of certain autonomous patient status applications 261 in the patient sensor packages 120. However, the greater processing and historical data storage capacity that may be available in care operations service suite 300, especially a shared COSS 132, make it possible to perform far more sophisticated and subtle detections.

While the examples shown may illustrate many individual modules as separate elements, one of ordinary skill in the art would recognize that these modules may be combined into a single functional block or element. One of ordinary skill in the art would also recognize that a single module may be divided into multiple modules.

III. Methods of Operation

FIGS. 4-10 illustrate a group of processes performed by a patient sensor package in a patient monitoring and communication system according to an exemplary embodiment of the invention. The processes may include startup and configuration, configuration management, connection management, location management, sensor management, presentation management, and autonomous application operation.

Figure 4:
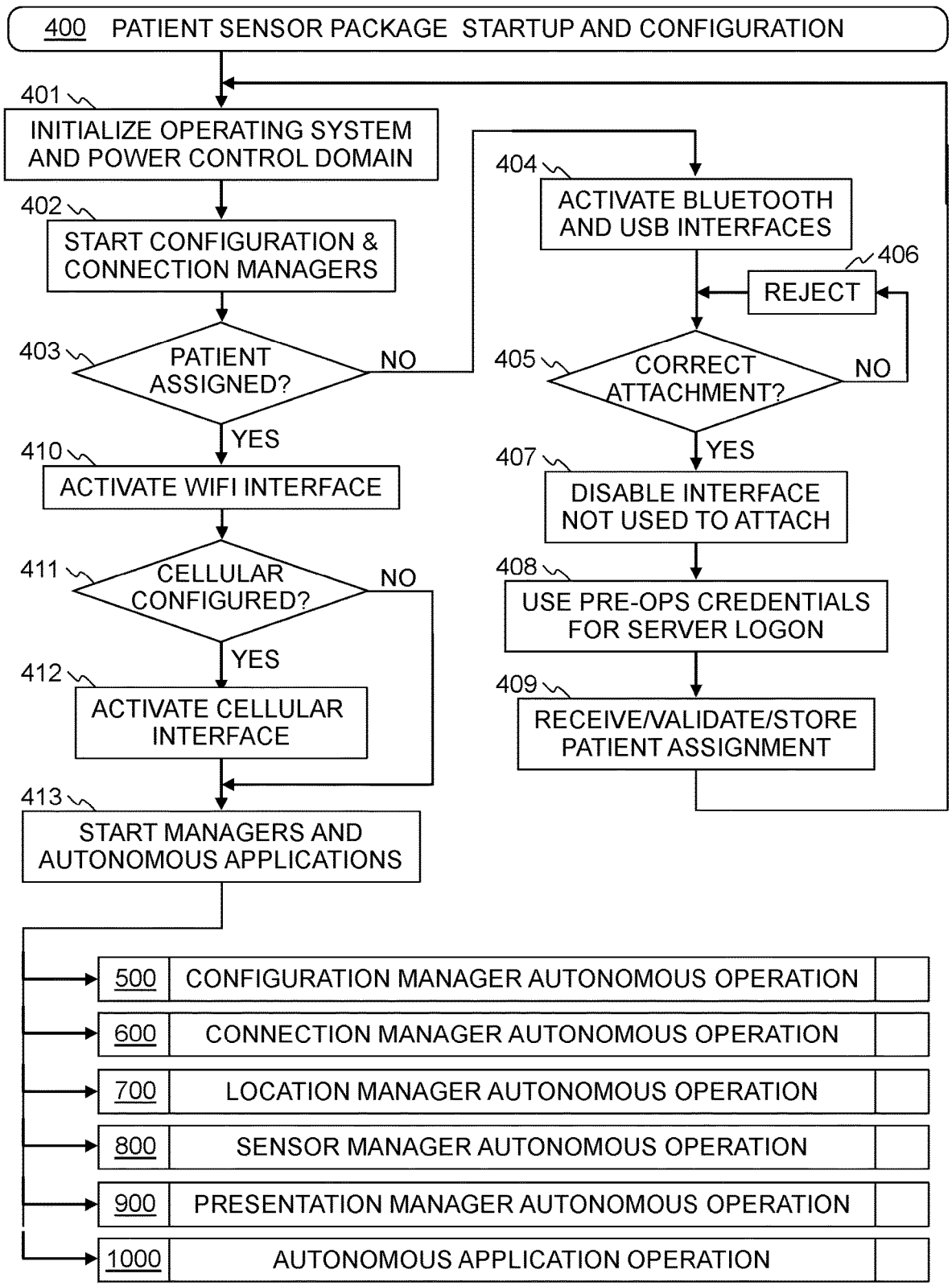
FIGS. 4-10 illustrate a group of processes performed by a patient sensor package in a patient monitoring and communication system according to an exemplary embodiment of the invention.

FIG. 4 provides detail of process 400, patient sensor package startup and configuration, which may generally occur after powering on or resetting a patient sensor package 120. The process begins with operation 401, in which the operating system and power control domain of patient sensor package 120 are initialized. Specific modules affected by this operation may include processor, memory, and operating system 201, as well as power control hardware and drivers 203. Operation 402 follows, which starts the configuration and connection managers 210 and 220. With these modules running, operation 403 can check databases 211 and determine whether this patient sensor package 120 has been assigned to a specific patient.

If not, operation 404 prepares the patient sensor package 120 to receive an assignment by activating its local configuration interfaces 112, which may be implemented as one or more of Bluetooth radio 223 and USB port 224. When an attachment attempt purporting to be from an administrator workstation 111 arrives on one of these ports, operation 405 determines whether the attempt is valid and authorized using information from databases 211 representing configured administrator credentials. If the attempt is not correct, operation 406 rejects it and further attempts may be awaited. If a correct attempt is received from an authorized administrator workstation 111, operation 407 may disable the port that wasn't used—that is, if the attachment attempt arrived via Bluetooth, operation 407 would disable the USB port, and vice versa. Subsequently, in operation 408 the patient sensor package 120 may use its pre-operational credentials to establish a secure log on session with the Care Operations Message Server 340 of a care operations service suite 300, and in operation 409 receive, validate, and (if valid) store in databases 211 the data associated with a patient assignment. Such data may include, without limitation, patient identity, patient preferences such as interface language, system preferences such as permitted communication modes, facility network access parameters/credentials, sensor monitoring and reporting schedules, and facility-specific or patient-specific autonomous patient status applications. After operation 409 is complete, process 400 starts over at operation 401 in order to act on the new configuration data in a pristine state.

If operation 403 determines that this patient sensor package 120 has been assigned to a patient, whether newly configured or otherwise, operation 410 activates Wifi radio 221 and attaches to a corresponding network 104 or 105 if available in order to facilitate interfaces 124 and 125, using corresponding parameters and credentials received as part of the patient assignment configuration. In addition, if operation 411 determines, again based on configuration data received with the patient assignment, that cellular connectivity is allowed, then operation 412 activates cellular radio 222 and attaches to a corresponding public network 105 if available in order to facilitate interface 152. Subsequently, operation 413 starts the remaining modules, including location, sensor, and presentation managers 230, 240, and 250 as well as autonomous patient status applications 261. Finally, process 400 segues into routine operation by initiating the autonomous operation processes associated with the manager and application modules; these autonomous operation processes 500, 600, 700, 800, 900, and 1000 are described hereinafter.

Figure 5:
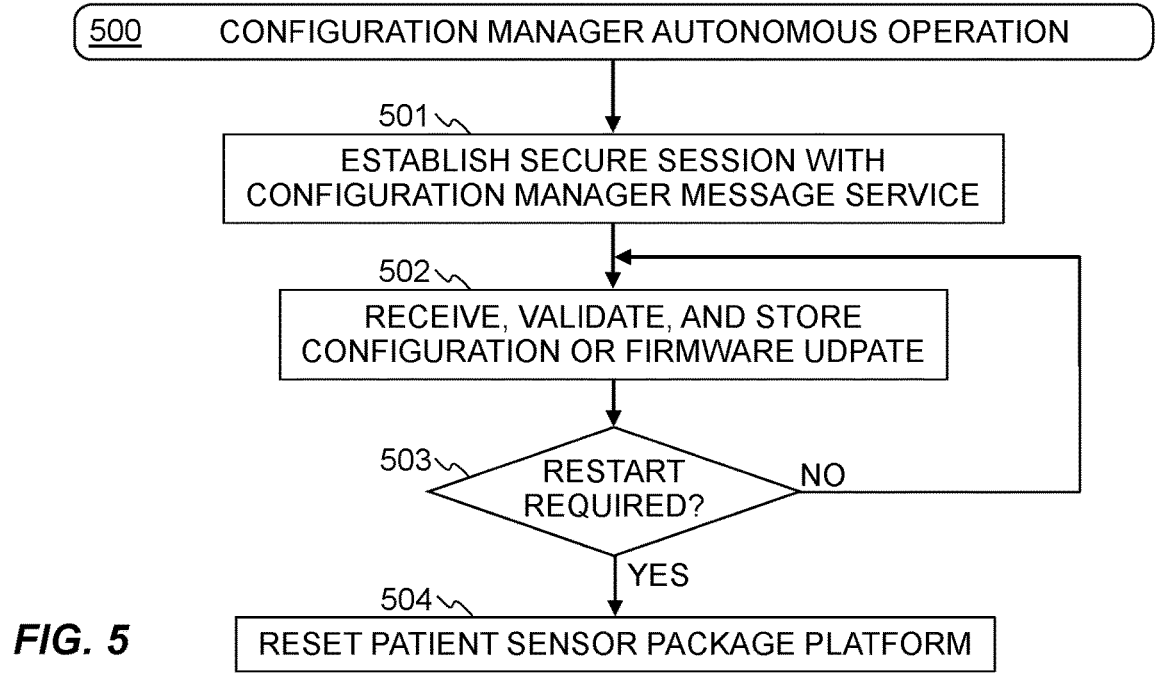

FIG. 5 provides detail of process 500, configuration manager autonomous operation. The process begins with operation 501, in which configuration manager 210 may establish a secure session with configuration manager message service 341 using configured mutual authentication credentials. Subsequently, at any time service 341 may send a configuration or firmware update to manager 210, causing operation 502 to receive, validate, and (if valid) store the update in databases 211. Operation 503 then detects whether the received update requires the patient sensor package 120 to reinitialize itself; if not, process 500 loops back to repeat indefinitely at operation 502, but if so operation 504 performs a clean shutdown of all patient sensor package 120 modules and resets the device to restart process 400.

Figure 6:
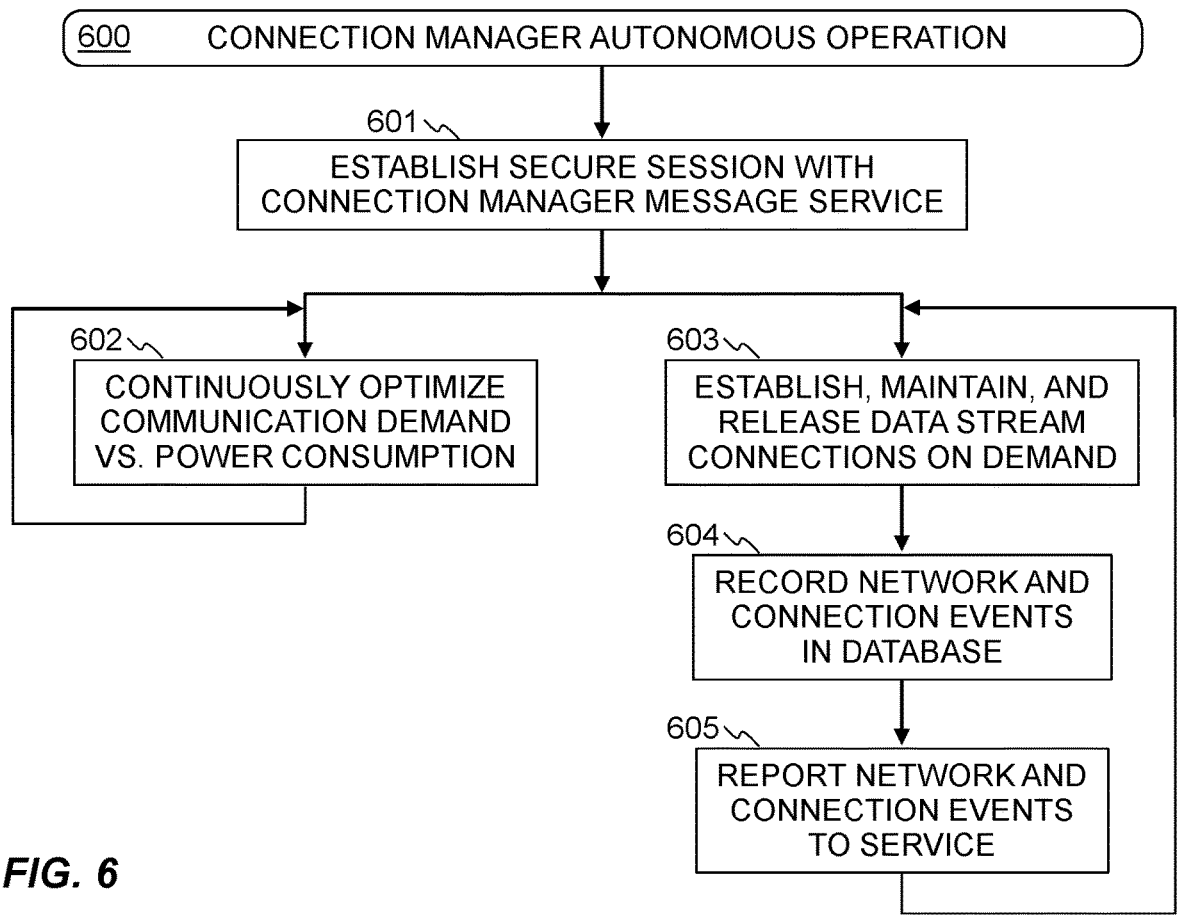

FIG. 6 provides detail of process 600, connection manager autonomous operation. The process begins with operation 601, in which connection manager 220 may establish a secure session with connection manager message service 342 using configured mutual authentication credentials. Subsequently, two interdependent threads may execute. In the first, operation 602 may continuously optimize communication continuity and interface hardware operation vs. power consumption according to configured reporting periodicity, battery life goals, and demand from both active applications and service 342. In the second, operation 603 may at any time establish, maintain, and release temporary data stream connections upon demand from monitoring applications 262 and communication applications 265; operation 604 may record network attachment, connection establishment, and related events in database 211; and operation 605 may report those recorded events to service 342 where appropriate. Process 600 loops back to repeat each thread indefinitely at operations 602 and 603 respectively.

Figure 7:
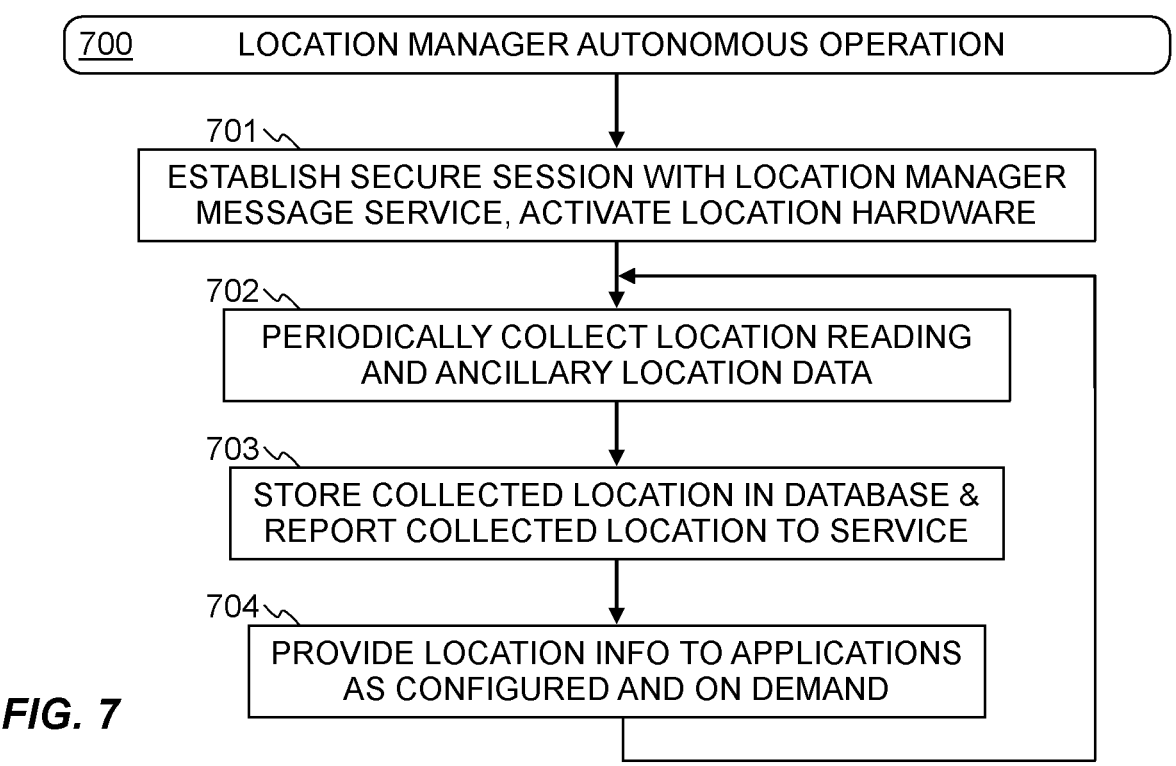

FIG. 7 provides detail of process 700, location manager autonomous operation. The process begins with operation 701, in which location manager 230 may establish a secure session with location manager message service 343 using configured mutual authentication credentials, and then activate any hardware modules specific to location determination such as GPS Radio 225. Subsequently, process 700 may loop continuously over the following three operations according to a configured periodicity. First, operation 702 may collect location readings via location stack 213 from GPS Radio 225 and ancillary location-relevant readings from other communication modules, sensors, and user interface devices. Operation 703 may store these location readings in databases 211, and report them to service 343 for further handling in care operations service suite 300. Finally, operation 704 may provide location information to applications in application suite 260, both asynchronously as configured and on demand.

Figure 8:
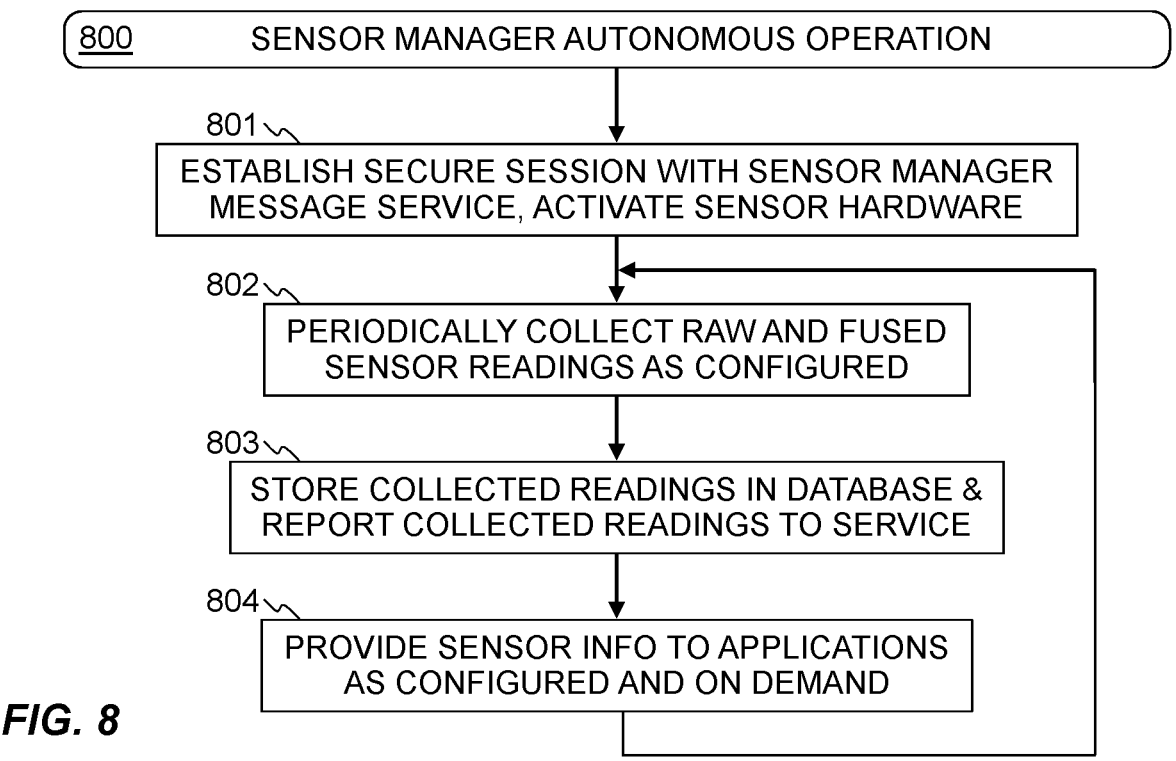

FIG. 8 provides detail of process 800, sensor manager autonomous operation. The process begins with operation 801, in which sensor manager 240 may establish a secure session with sensor manager message service 344 using configured mutual authentication credentials, and then activate any and all configured sensor hardware modules. Subsequently, process 800 may loop continuously over the following three operations according to a configured periodicity and as configured for each sensor. First, operation 802 may collect raw and fused sensor readings via sensor fusion stack 214. Operation 803 may store these sensor readings in databases 211, and report them to service 344 for further handling in care operations service suite 300. Finally, operation 804 may provide sensor information to applications in application suite 260, both asynchronously as configured and on demand.

Figure 9:
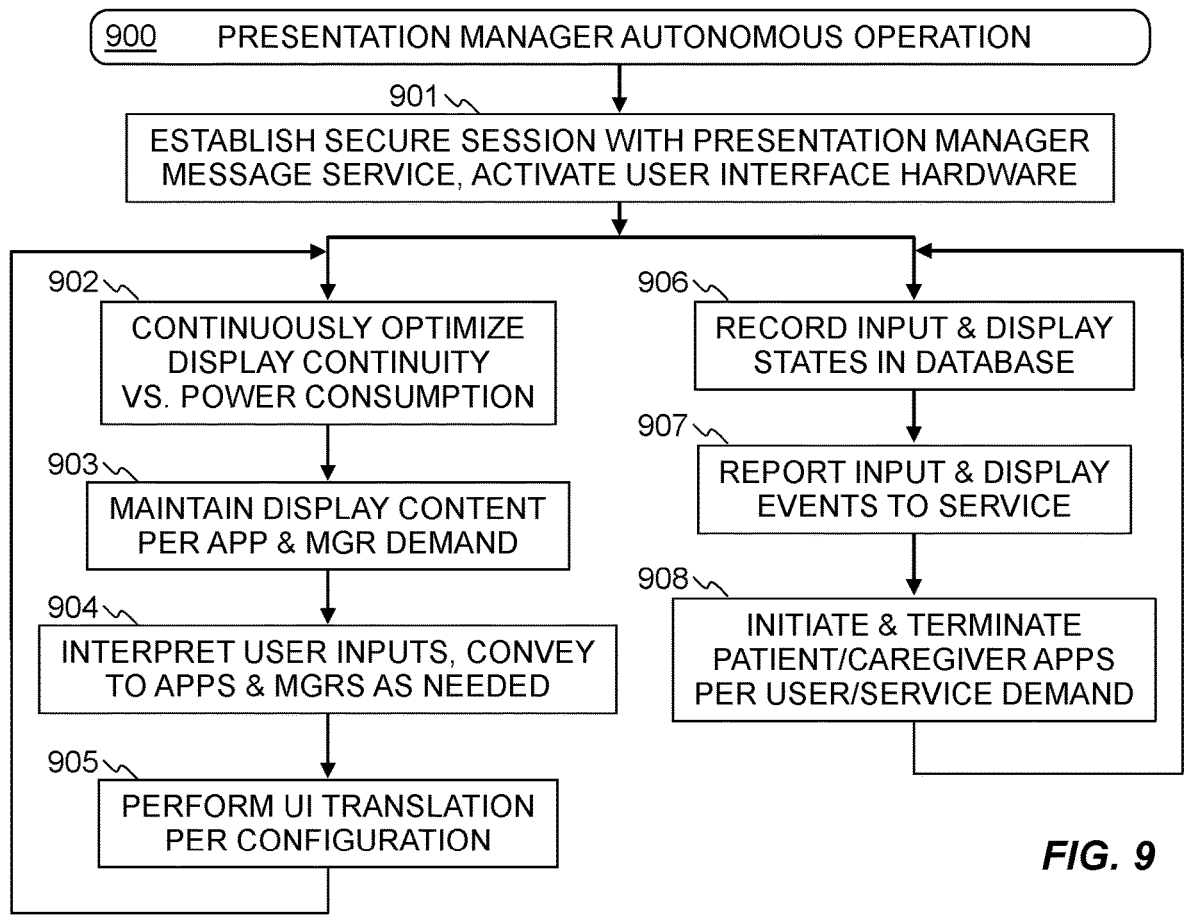

FIG. 9 provides detail of process 900, presentation manager autonomous operation. The process begins with operation 901, in which presentation manager 250 may establish a secure session with presentation manager message service 345 using configured mutual authentication credentials, and then activate any and all configured user interface hardware modules. Subsequently, multiple interdependent threads may execute, with each looping over its own set of operations. As shown, in the first thread operation 902 may continuously optimize display continuity and user interface hardware operation vs. power consumption according to configured display persistence, battery life goals, and user demand from both active applications and service 345. Operation 903 may maintain display content such as screen and audio buffers according to application, manager, and service demands. Operation 904 may interpret user interface inputs and convey them to applications and managers according to their registered needs. Finally, operation 905 may, if enabled, perform user interface translation functions according to configured patient preferences.

As shown, in the second thread operation 906 may record user interface inputs and output state changes in databases 211, while operation 907 may report those input events and output state changes to service 345. Finally, operation 908 may initiate and terminate patient-controlled applications 264 and 265 according to user interface inputs, as well as initiate and terminate caregiver-controlled applications 262 and 263 according to service 345 commands. Process 900 loops back to repeat each thread indefinitely, as shown at operations 902 and 906 respectively. Note that the specific allocation of operations to threads shown in FIG. 9 is exemplary; more or fewer threads may be used, with different arrangements of the operations among them.

Figure 10:
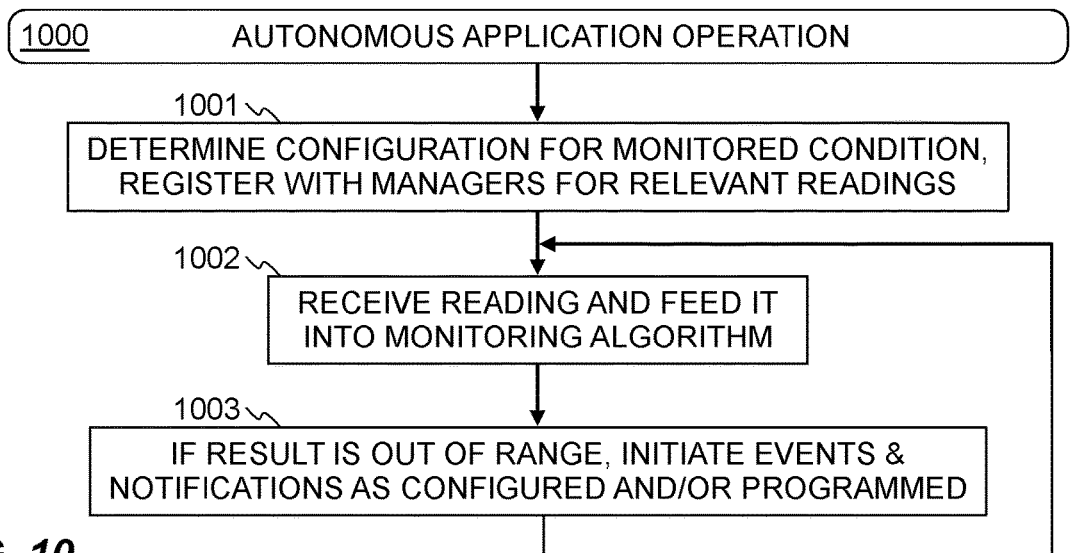

FIG. 10 provides detail of process 1000, autonomous application operation. This process is a generalization of multiple specific autonomous patient status applications 261, which may all perform similarly while acting upon different data and triggering different actions. Process 1000 begins with operation 1001, in which the specific autonomous patient status application 261 may read its configuration to determine which sensors or other data to monitor, as well as ranges for conditions of interest, and register with the various managers, such location manager 230 and sensor manager 240, for readings relevant to those conditions. Subsequently, process 1000 may loop continuously over the following operations according to a configured periodicity and as configured for each condition. First, operation 1002 may receive a reading and feed it into its monitoring algorithm. For example, an algorithm may compute a hysteresis or an average as appropriate for the condition and according to a configured sensitivity, and compare the result to a corresponding range. If the algorithm's result indicates an out of range condition, operation 1003 may initiate events and/or notifications as configured and/or programmed.

Figure 11:
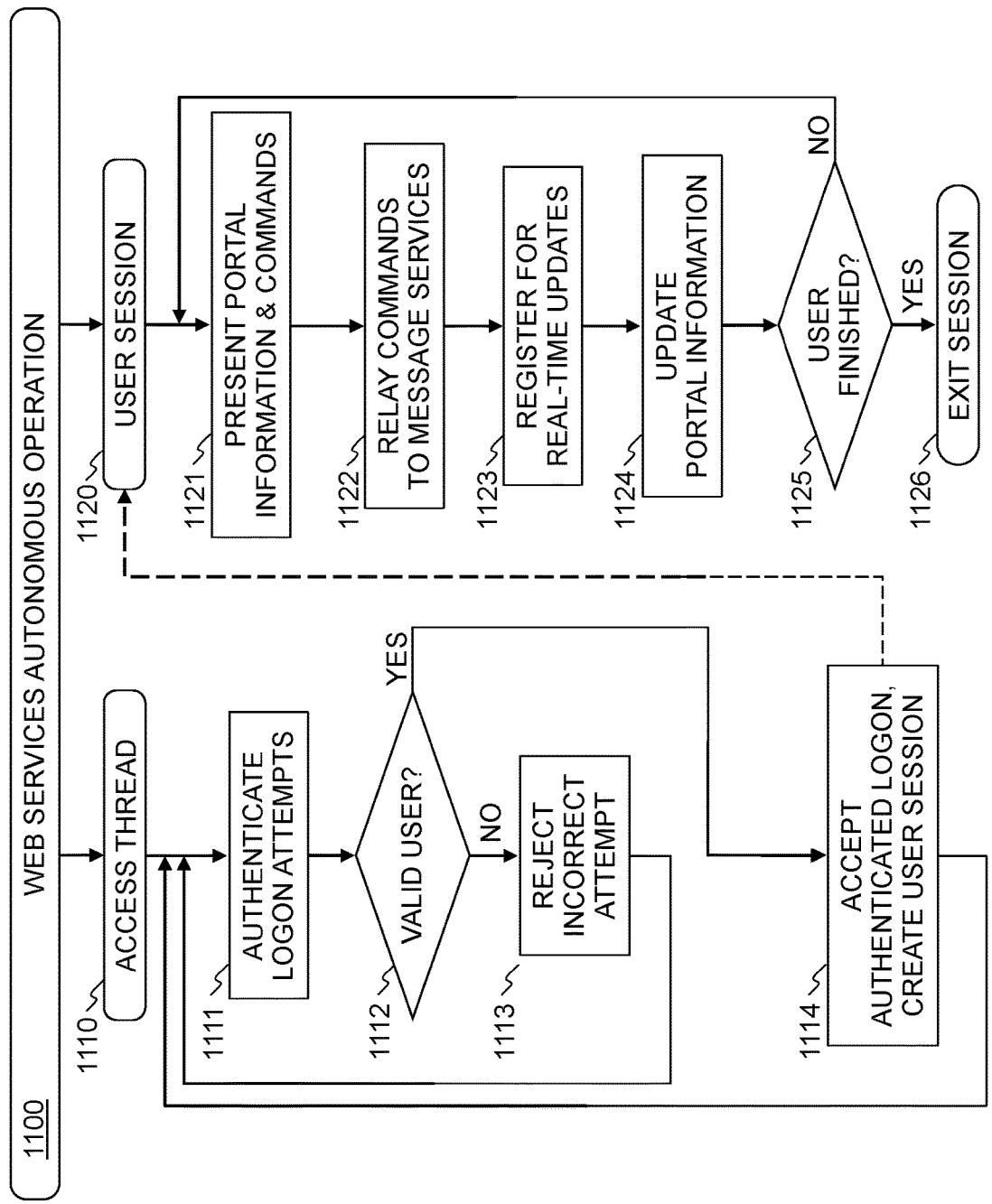
FIGS. 11-13 illustrate a group of processes performed by a care operations service suite in a patient monitoring and communication system according to an exemplary embodiment of the invention.
Figure 12:
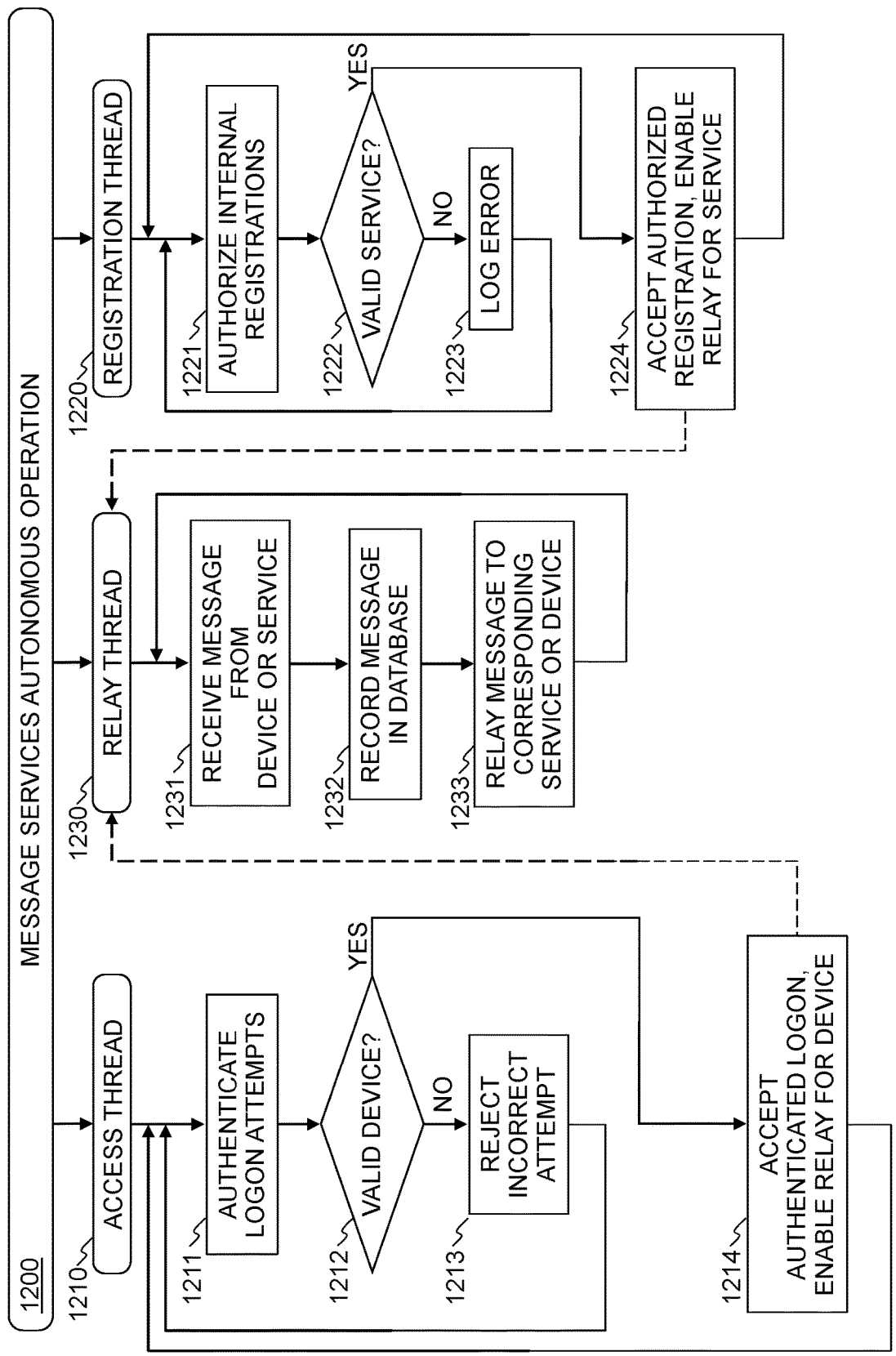
Figure 13:
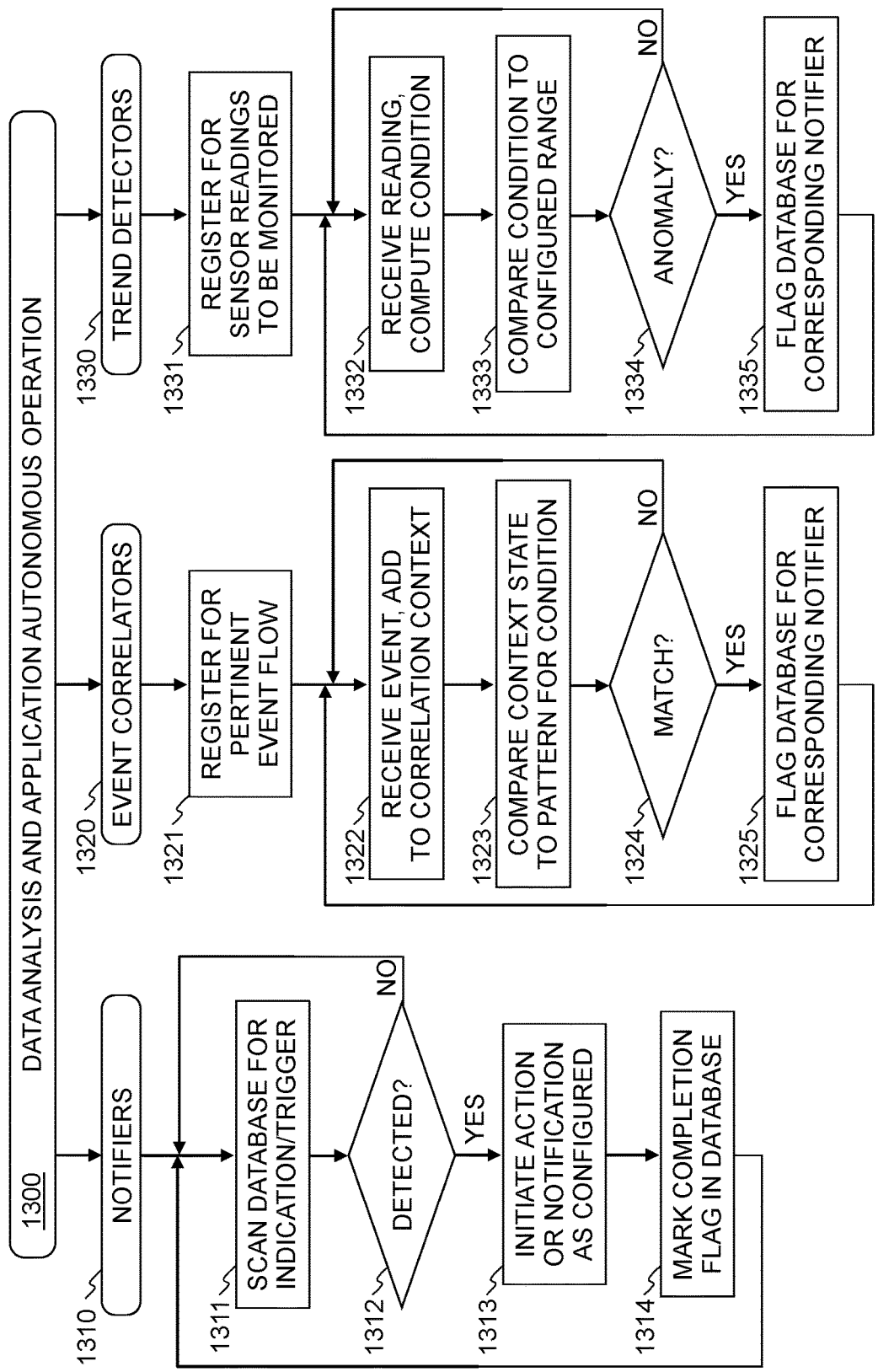

FIGS. 11-13 illustrate a group of processes performed by a care operations service suite in a patient monitoring and communication system according to an exemplary embodiment of the invention. The processes may include web services operation, message services operation, data analysis (notification), data analysis (event identification), and data analysis (trend detection).

FIG. 11 provides detail of process 1100, web services autonomous operation. Care operations web server 330 may execute this process in support of its job providing the four types of user portal web service—administrator portal 331, caregiver portal 332, patient portal 333, and family portal 334. One primary thread is executed continuously by this process, access thread 1110. Zero, one, or more than one user session 1120 may also execute temporarily while a portal user is logged on. Temporal flow within a thread is represented by solid arrows, while temporal relationships between the threads are represented by dashed arrows.

Access thread 1110 executes continuously throughout the life of a care operations service suite 300 and its care operations web server 330. In operation 1111, it detects logon attempts purporting to be from authorized users, and authenticates them. If it determines at operation 1112 that the logon attempt does not represent a valid user, then at operation 1113 the server rejects the incorrect attempt and continues the process from the beginning. Otherwise, if the logon attempt represents a valid user, then at operation 1114 the server will accept the authentic logon and create a user session 1120. Multiple user sessions 1120 may exist simultaneously, each one representing and supporting a separate user, and taking on the portal type required for that user. Upon creating a user session 1120, access thread 1110 loops back to operation 1111 for the next logon attempt.

A user session 1120 thus created provides a context in which the portal user may perform the various activities permitted to the corresponding user type; it executes independently of any other user session as well as the continuous access thread. At operation 1121, the session may present the portal user interface, which may include the user's information dashboard as well as a set of commands that may be available. For example, a caregiver user may see a list of assigned patients and one or more critical indicators for each, such as location, heart rate, or other health status, along with commands for monitoring specific sensors in real time and communicating with the patient or corresponding family members, while a family member may see a subset of health and status information regarding only the related patient, along with caregiver contact information and, if permitted, commands for communicating with the patient or caregiver. Operation 1122 may in turn respond to selected commands by relaying them to the corresponding message service or gateway for processing either within care operations service suite 300 or at the pertinent patient sensor package 120. If commanded explicitly or if configured by preference to do so automatically when a session starts, operation 1123 may register with one or more of the message services to receive real-time updates from any associated patient sensor package or packages. Upon receiving new information to display, whether as the result of a requested command or asynchronously due to a subscribed update such as a sensor reading, operation 1124 may update the portal information presented to the user. If the session detects at operation 1125 that the user is finished, perhaps via an explicit logoff command or an inactivity timer that causes an implicit logoff, the session terminates at operation 1126. Otherwise, user session 1120 may repeat until then.

FIG. 12 provides detail of process 1200, message services autonomous operation. Care operations message server 340 may execute this process in support of its job providing the five types of message service—configuration manager 341, connection manager 342, location manager 343, sensor manager 344, and presentation manager 345. An implementation may provide one copy of this process, specializing its operation for each service depending on the source, destination, or nature of each arriving event. Alternatively, an implementation may provide a separate copy of this process for each service. Regardless, message services autonomous operation process 1200 features three interdependent threads executing continuously: access thread 1210, registration thread 1220, and relay thread 1230. Temporal flow within a thread is represented by solid arrows, while temporal relationships between the threads are represented by dashed arrows.

Access thread 1210 is responsible for processing message service logon attempts from manager modules 210, 220, 230, 240, and 250 in patient sensor packages 120. It is the server-side correspondent to operations 501, 601, 701, 801, and 901 when one of them is performed by a patient sensor package 120. Access thread 1210 executes continuously throughout the life of a care operations service suite 300 and its care operations message server 340. In operation 1211, it detects logon attempts purporting to be from legitimate managers 210, 220, 230, 240, and 250 in authorized patient sensor packages 120, and authenticates each request. If it determines at operation 1212 that the logon attempt does not represent a valid device and manager, then at operation 1213 the server rejects the incorrect attempt and continues the process from the beginning. Otherwise, if the logon attempt represents a valid device and manager, then at operation 1214 the server will accept the authentic logon and enable message relay for that manager. Access thread 1210 then loops back to operation 1211 for the next logon attempt.

Registration thread 1220 is responsible for processing portal user sessions' requests for real-time updates of information from patient sensor packages (120). It is the message service correspondent of web services operation 1123 previously described. Registration thread 1220 executes continuously throughout the life of a care operations service suite 300 and its care operations message server 340. In operation 1221, it detects registration requests purporting to be from a legitimate user session 1120 in a portal web service 331, 332, 333, or 334 of the same care operations service suite 300, and authenticates each request. If it determines at operation 1222 that the registration attempt does not represent a valid service, then at operation 1223 the server logs an internal error describing the incorrect attempt and continues the process from the beginning. Otherwise, if the registration attempt represents a valid service, then at operation 1224 the server will accept the authentic registration and enable message relay for that service. Registration thread 1220 then loops back to operation 1221 for the next registration attempt.

Relay thread 1230 is responsible for the meat of the process, which is to move messages between authorized managers at valid patient sensor packages 120 and registered services as well as gateways 360 and 370 within care operations service suite 300, thereby facilitating communication among them and enabling their respective features. A single instance of relay thread 1230 may execute continuously throughout the life of a care operations service suite 300 and its care operations message server 340, acting on messages that match the managers and services for which message relay has been enabled. Alternatively, a separate instance of relay thread 1230 may be created for each relay-enabled manager and service, and execute continuously only for the duration the correspondent has been thus enabled. Either way, the operations performed are the same. In operation 1231, relay thread 1230 may receive a message from a relay-enabled manager 210, 220, 230, 240, and 250 in a patient sensor package 120 (for which "device" is shorthand in the figure), service 331, 332, 333, or 334 in care operations service suite 300, or gateway 360 or 370 in care operations service suite 300. Operation 1232 then records the incoming message in databases 350, and operation 1233 relays the message to its corresponding destination or destinations—one or more services or gateways if received from a device, service, or gateway; a device if received from a service or gateway. Relay thread 1230 then loops back to operation 1231 for the next message to process.

Note that a message from a device may contain a sensor or location reading, a user interface input or output state change, a communication request, or any other event, while a message from a service or gateway may contain a portal command, a communication request, a configuration update, or any other event. Example actions may include relaying messages containing location and sensor readings from patient sensor packages 120 to corresponding registered portal web service sessions 1120 for display to associated caregivers or family members; relaying messages containing presentation updates (user interface inputs or output state changes) from corresponding registered portal web service sessions 1120 to patient sensor packages 120 so patients may be presented information their associated caregivers or family members may want them to know; relaying messages containing presentation updates (user interface inputs or output state changes) from patient sensor packages 120 to corresponding registered portal web service sessions 1120 so associated caregivers or family members may monitor patients' activities; relaying configuration messages between patient sensor packages 120 and corresponding registered administrator portal web service sessions 1120; relaying connection messages among patient sensor packages 120, corresponding registered portal web service sessions 1120, and connection gateway 360; and numerous other scenarios that may be inferred or extrapolated from the combination of activities described herein.

FIG. 13 provides detail of process 1300, data analysis and application autonomous operation. Autonomous data analysis and application support platform 380 may execute this process as it hosts the various notification initiators 381, diagnostic event correlators 382, and diagnostic trend detectors 383. These three types of data analyzers and applications are manifested in process 1300 as independent subprocesses, respectively notifiers 1310, event correlators 1320, and trend detectors 1330. Each subprocess type may be instantiated multiple times, once for each specific notifier, correlator, or detector analyzing distinct conditions or executing distinct actions according to its configuration and programming. As well, each subprocess may execute continuously once instantiated.

In notifiers subprocess 1310, operation 1311 periodically scans databases 350 for the specific indications or trigger data settings that the notifier 381 is configured or programmed to notice. Such indications or triggers may be as simple as a flag set by an event correlator 382 or trend detector 383, or as complex as a multi-variable state arising from multiple sources; however, they may be generally based on instantaneous states, rather than time-series event analysis. Upon detection of the indication or trigger in operation 1312, operation 1313 may initiate the programmed action or send the configured notification to one or more configured recipients. At operation 1312, if there is no detected trigger, then the process loops back to operation 1311 for the next trigger, and repeats as often or as long as needed. Operation 1314 may then mark a completion flag in databases 350, effectively logging the event. This completion flag may also play into the detection algorithm to avoid excessive notifications or repetitive actions as appropriate. Subprocess 1310 may then loop back to operation 1311 to repeat according to the specific notifier's configured periodicity.

An event correlator 382, on the other hand, may carry out time-series event analysis, allowing very complex situations to be identified. For example, a fall-detection correlator might examine accelerometer readings and location readings, coupled with heart-rate readings and communication events, to determine that a patient has fallen suddenly and then neither gotten back up nor placed a call for help, while distinguishing this from simply having gone to bed. Event correlators subprocess 1320 starts with operation 1321, which may register with autonomous data analysis and application support platform 380 to receive a flow of pertinent events such as sensor readings, location readings, user input events, communication events, and so forth. Once events are flowing into the correlator 382, operation 1322 receives each event and adds it to the correlation context according to its programmed algorithm. Then operation 1323 may compare the new correlation context state to a pattern programmed or configured for the specific correlator 382. If a match is detected in operation 1324, operation 1325 may set a flag in databases 350 so an allied notifier 381 may notice the indication and perform a corresponding action or send an appropriate notification. Whether or not the target condition is found, event correlators subprocess 1320 then loops back to operation 1322 to repeat this sequence for each incoming event. Note that a single correlator may maintain and distinguish multiple correlation contexts, one for each patient or caregiver or whatever it is observing; alternatively, multiple instances of event correlators subprocess 1320 may exist for a particular kind of event correlator 382, with each subprocess instance encapsulating the correlation context for a particular patient, caregiver, or other entity.

Similarly, a trend detector 383 may perform time-series analysis on a stream of sensor readings or other recurring data, allowing anomalies to be identified or even predicted. For example, an angina predictor may collect heart rate and blood pressure readings to warn patients when they may be approaching an excessive activity level. Trend detectors subprocess 1330 starts with operation 1331, which may register with autonomous data analysis and application support platform 380 to receive a flow of pertinent sensor readings. Once these readings are flowing into the detector 383, operation 1332 receives each reading and computes the corresponding condition according to its programmed algorithm and configured sensitivity levels. An algorithm may be as simple as averaging or Kalman filtering a single sensor's measurements, or it may be a significantly more complex combination of multiple sensors with hysteresis ranges and other factors. Operation 1333 may then compare the computed condition to a range configured for the specific detector 383. If an anomaly is detected in operation 1334, operation 1335 may set a flag in databases 350 so an allied notifier may notice the indication and perform a corresponding action or send a corresponding notification. Whether or not the target condition is found, trend detectors subprocess 1330 then loops back to operation 1332 to repeat for each incoming reading. Note that a single detector may maintain and distinguish multiple conditions, one for each patient whose sensor(s) it is monitoring; alternatively, multiple instances of trend detectors subprocess 1330 may exist for a particular kind of trend detector 383, with each subprocess instance encapsulating the condition for a particular patient.

FIGS. 14-23 illustrate a group of processes distributed across multiple elements in a patient monitoring and communication system according to an exemplary embodiment of the invention. The processes may include administrator management, caregiver management, patient management, family member management, patient tracking by a caregiver, and patient tracking by a family member.

Figures 14, 15, 16:
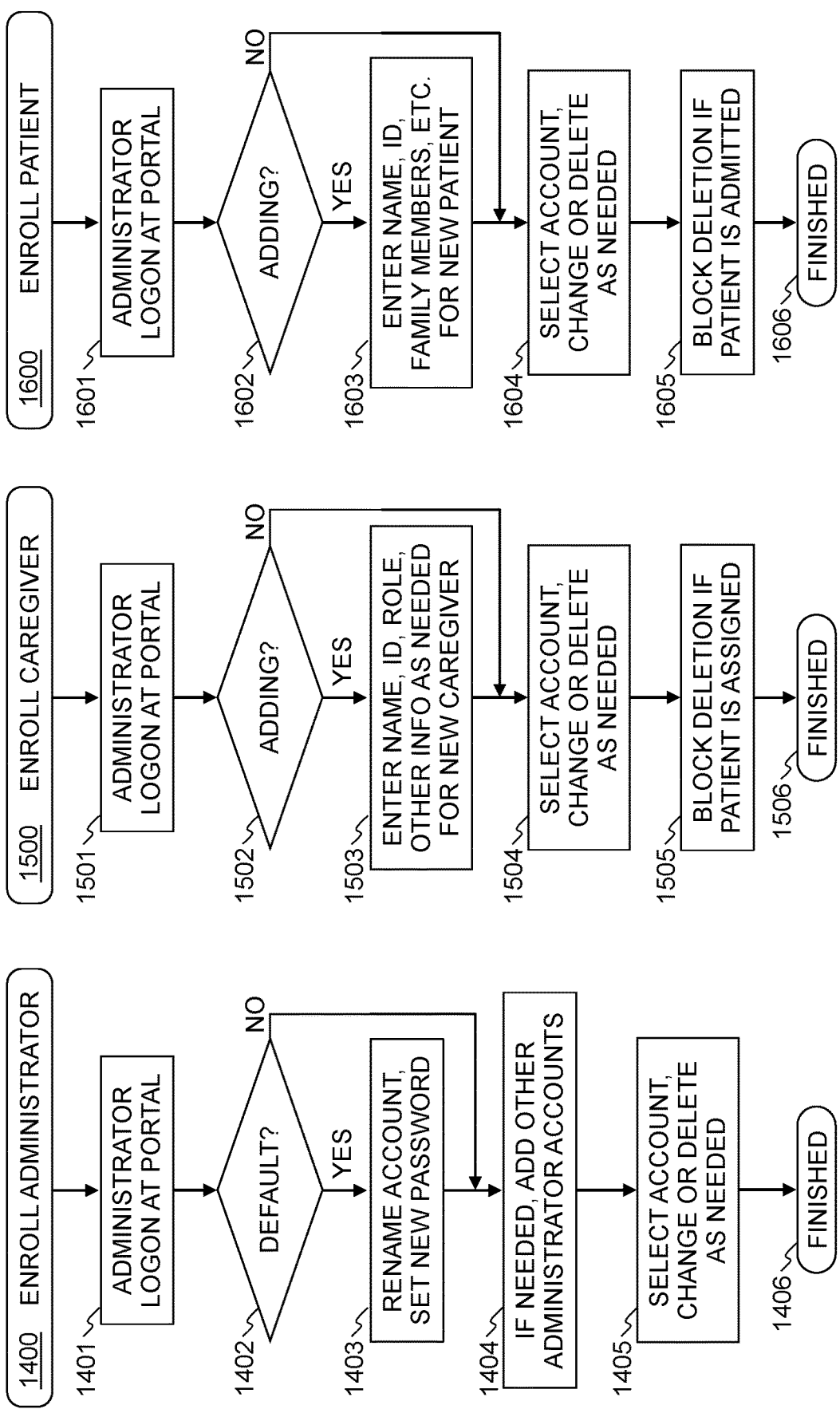

FIG. 14 provides detail of enroll administrator process 1400, whereby an administrator user may add, change, or delete one or more other administrator users. Enroll administrator process 1400 begins with operation 1401, in which an administrator user may log on using the administrator portal web service 331. Note that a new care operations service suite 300 may have a default administrator user account defined, providing a foundation whereby other user accounts may be created. Operation 1402 checks whether it was this default administrator account that was used for the current logon, and if so in operation 1403 the user is required to rename the account from that of the default to that of this initial administrator user, and to change the account's password. Once that is done, or if the logged-on administrator user is not the default administrator, in operation 1404 the logged-on administrator may add other administrator accounts by providing names, identifiers, and other appropriate information to create their accounts. If changes are needed to an existing administrator user account, in operation 1405 the logged-on administrator may select the desired account and change its information or delete it as appropriate. Process 1400 then finishes at operation 1406. Note that Process 1400 may be repeated as many times as necessary to make multiple changes; operation 1401 may be skipped if the administrator user is already logged on.

FIG. 15 provides detail of enroll caregiver process 1500, whereby an administrator user may add, change, or delete one or more caregiver users. Enroll caregiver process 1500 begins with operation 1501, in which an administrator user may log on using the administrator portal web service 331. If the logged-on administrator user is adding a caregiver, determined at operation 1502, in operation 1503 the logged-on administrator may enter name, identifier, caregiving role (doctor, nurse, pharmacist, therapist, etc.), work times, and other appropriate information to create the account. If changes are needed to an existing caregiver user account, in operation 1504 the logged-on administrator may select the desired account and change its information or delete it as appropriate. Operation 1505 may block the deletion of a caregiver account if a patient is assigned to the caregiver, thereby ensuring integrity of the system's representation of that relationship. Process 1500 then finishes at operation 1506. Note that Process 1500 may be repeated as many times as necessary to make multiple changes; operation 1501 may be skipped if the administrator user is already logged on.

FIG. 16 provides detail of enroll patient process 1600, whereby an administrator user may add, change, or delete one or more patient users. Enroll patient process 1600 begins with operation 1601, in which an administrator user may log on using the administrator portal web service 331. If the logged-on administrator user is adding a patient, determined at operation 1602, in operation 1603 the logged-on administrator may enter name, identifier, family members, medical conditions, and other appropriate information to create the account. If changes are needed to an existing patient user account, in operation 1604 the logged-on administrator may select the desired account and change its information or delete it as appropriate. Operation 1605 may block the deletion of a patient account if the patient is still admitted to the institution using care operations service suite 300 and has caregiver relationships defined or resources assigned, thereby ensuring integrity of the system's representation of those relationships. Process 1600 then finishes at operation 1606. Note that Process 1600 may be repeated as many times as necessary to make multiple changes; operation 1601 may be skipped if the administrator user is already logged on.

Figure 17:
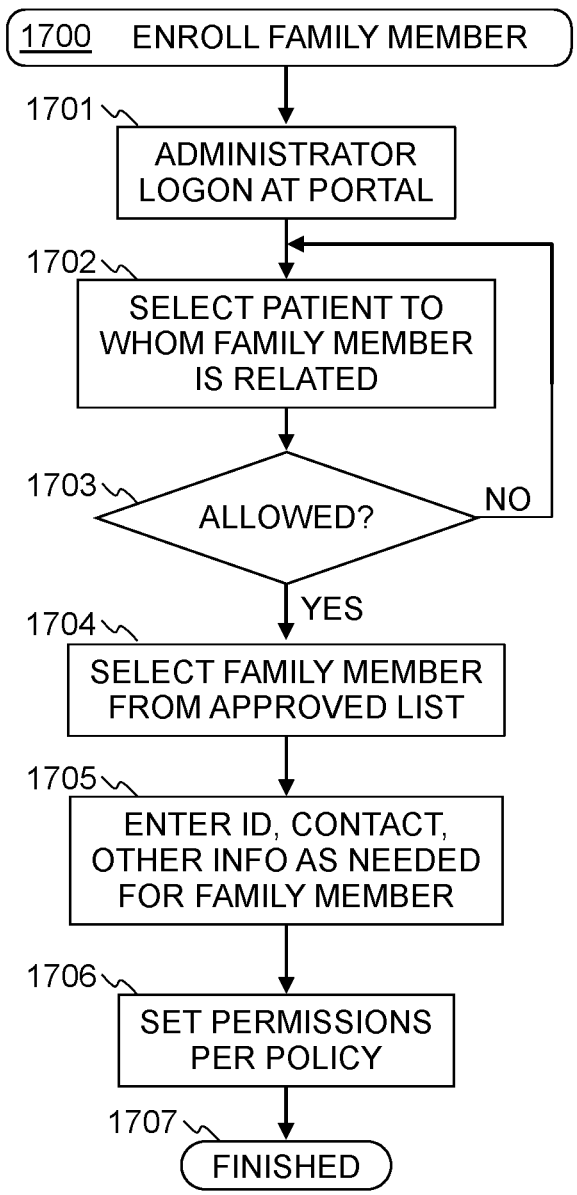

FIG. 17 provides detail of enroll family member process 1700, whereby an administrator user may add, change, or delete one or more family member users associated with a patient user. Enroll family member process 1700 begins with operation 1701, in which an administrator user may log on using the administrator portal web service 331. In operation 1702 the logged-on administrator user may select the patient to whom the family member to be administered is related. Operation 1703 determines whether the patient account information indicates that a family member has been identified and is permitted to have a user account for participating in the selected patient's care. If not, process 1700 returns to operation 1702 so the administrator may select a different patient. Also, separate from the explicit operations in process 1700, the administrator may follow up with the patient and his or her family to verify whether their intent is properly represented in the system. If a family member is allowed to participate in the selected patient's care, in operation 1704 the logged-on administrator user may select a specific family member from the approved list associated with the selected patient, and in operation 1705 enter identifier, contacts, and other information as appropriate to add, change, or delete the family member's user account. Note that family members may be listed in the patient's account who are not permitted to participate in care by having a family member user account; these people would not be selectable in operation 1704, even if they are visible. Then in operation 1706 the system may automatically set permissions for what information the family member user can see and what actions the family member user can perform in the family member portal web service 334, based on facility policy settings configured through management services. Process 1700 then finishes at operation 1706. Note that Process 1700 may be repeated as many times as necessary to make multiple changes; operation 1701 may be skipped if the administrator user is already logged on.

FIG. 18 provides detail of admit patient process 1800, whereby an administrator user may activate a patient in care operations service suite 300 and assign resources to support the patient's care. Process 1800 begins with operation 1801, in which an administrator user may log on using the administrator portal web service 331. In operation 1802 the logged-on administrator may select an enrolled patient and mark the patient admitted, then assign resources including one or more caregivers, room numbers, equipment identifiers, and so forth. In operation 1803, associated family member accounts may be activated, if any exist. In operation 1804, the administrator may select an idle patient sensor package 120, attach it to administrator workstation 111, and initiate configuration so as to assign the selected patient sensor package 120 to the admitted patient, thereby also inducing patient sensor package startup and configuration process 400. When configuration is complete, in operation 1805 the admitting administrator or a caregiver may detach the now-assigned patient sensor package 120 from administrator workstation 111 and attach it to the admitted patient's body as appropriate to the device's form (that is, to the patient's wrist, chest, head, or whatever). Process 1800 then finishes at operation 1806. Note that in an embodiment, admit patient process 1800, enroll patient process 1600, and enroll family member process 1700 may be independent of one another, integrated with one another, or both; if integrated, their operations may be consecutively ordered, or intermingled in any usable manner.

FIG. 19 provides detail of discharge patient process 1900, whereby an administrator user may deactivate a patient in care operations service suite 300 and free the resources that were supporting the patient's care, typically upon permanent departure of the patient from the facility. Process 1900 begins with operation 1901, in which an administrator user may log on using the administrator portal web service 331. In operation 1902 the logged-on administrator may select an admitted patient and mark the patient discharged. In operation 1903, any associated family member accounts may be deactivated as well, then in operation 1904 the assigned resources (caregivers, room numbers, equipment, etc.) may be released for assignment to other patients. In operation 1905, the assigned patient sensor package 120 is also marked free, thereby inducing a configuration change removing the patient assignment information from patient sensor package 120 and returning it to the idle state; this deconfiguration operation may also command patient sensor package 120 to turn itself off. In operation 1906, the administrator or a caregiver may remove the patient sensor package 120 from the discharged patient and return it to the storage area for idle devices, which may include placing it in a charging station 121. Process 1900 then finishes at operation 1906. Note that in an embodiment, discharge patient process 1900, the delete action of enroll patient process 1600, and the delete action of enroll family member process 1700 may be independent of one another, integrated with one another, or both; if integrated, their operations may be consecutively ordered, or intermingled in any usable manner.

FIG. 20 provides detail of internal patient transfer process 2000, whereby an administrator user may move a patient from one caregiver, room, or other resource to another in the same facility. This procedure may also be used to establish a monitored outpatient status, in which the patient leaves the facility either temporarily or permanently but continues to wear the assigned patient sensor package and receive care remotely. Process 2000 begins with operation 2001, in which an administrator user may log on using the administrator portal web service 331. The logged-on administrator may then in operation 2002 select an admitted patient, and in operation 2003 change the assigned resources. Process 2000 then finishes at operation 2004.

Figure 21:
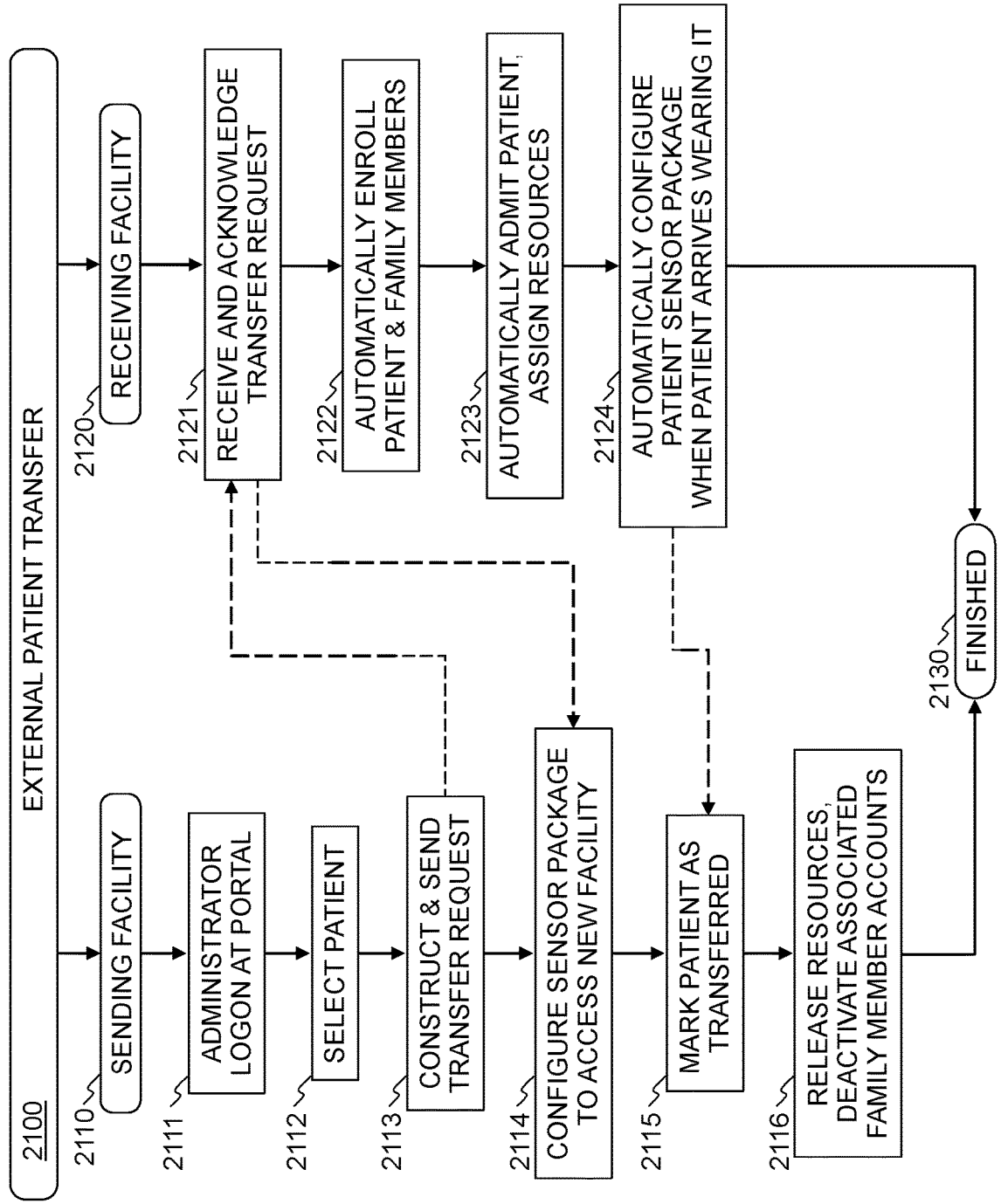

FIG. 21 provides detail of external patient transfer process 2100, whereby an administrator user may move a patient from one facility to another. Each facility is represented in the figure as an execution thread, with sending facility 2110 comprising the operations performed where the patient is leaving and receiving facility 2120 comprising the operations performed where the patient is going. Both facilities may be served by the same care operations service suite 300, in which case the interactions between these two threads (represented by dashed arrows in the figure) happen internally within that single care operations service suite 300. Alternatively, the two facilities may be served by different care operations service suites 300, in which case the interactions occur across a network between them, and may be facilitated and secured by their respective external information database gateways 370. Process 2100 begins with operation 2111 in sending facility 2110, in which an administrator user may log on using the administrator portal web service 331. The logged-on administrator may then in operation 2112 select an admitted patient and command the transfer. In operation 2113 the sending facility's care operations service suite 300 may then construct a transfer request message containing information about the patient—which may include the patient's enrollment data, medical data, sensor history, type and number of current resource assignments (but not specific resource identities), and identities of active family member user accounts—and send the transfer request message to the receiving facility's care operations service suite 300. Receiving facility 2120 may receive and acknowledge the request in operation 2121, providing its network access credentials to sending facility 2110 in the acknowledgement. Receiving facility 2120 may then automatically enroll the patient and corresponding family members in operation 2122 and admit the patient and assign the necessary resources in operation 2123, based on information received in the transfer request. Meanwhile, the sending facility 2110 may receive the acknowledgement and in operation 2114 automatically configure the patient's sensor package 120 with the receiving facility's network access credentials from the acknowledgement. At this point the patient may move from one facility to the other, and in operation 2124 the care operations service suite 300 at receiving facility 2120 may detect the patient's arrival when the corresponding patient sensor package 120 accesses the network there, whereupon additional configuration information may be pushed to the device; for example, certain policies and care applications may be different between the two facilities, necessitating configuration changes. Notice of the patient's arrival may also be sent to sending facility 2110, at which point the patient's status may be recorded as transferred in operation 2115, and assigned resources may be released and associated family member accounts may be deleted in operation 2116. Process 2100 then finishes at operation 2130.

FIG. 22 provides detail of caregiver track patient process 2200, whereby a caregiver may monitor or communicate with a specific patient. Process 2200 begins with operation 2201, in which a caregiver user may log on using the caregiver portal web service 332. The logged-on caregiver may then in operation 2202 select a patient whose care has been assigned to the caregiver, and view the patient information and available commands presented by portal 332.

Depending on the caregiver's role and permissions, the dashboard thus presented may provide a vast array of patient status information, including without limitation real-time sensor readings such as heart rate, temperature, blood pressure, location, and others; sensor reading history, including time-series graphs or tables; notifications sent or received regarding the patient and any related medicines, conditions, environment, or other matters; summaries of and access to complete medical records; resources assigned such as room, equipment, specialists, and others, along with their respective locations or availability schedules; a view of the latest display content from the active patient sensor package 120, showing what the patient sees; and status of ongoing command execution. Similarly, and again depending on the caregiver's role and permissions, the dashboard may also provide buttons, menus, and other command forms providing the ability to initiate various actions, including without limitation selecting or entering a notification and pushing it to the assigned patient sensor package 120 for display; altering notification thresholds for sensor readings; initiating or terminating audio or video monitoring of the patient via the assigned patient sensor package 120; exchanging text messages with the patient or a logged-on family member; initiating or terminating an audio-only or an audio and video connection to converse with the patient or a logged-on family member; and entering status and observation notes into the patient's medical record.

Given this universe of options, in operation 2203 the caregiver may initiate a permitted action or command, and in operation 2204 the portal web service 332 may log the action in databases 350 and relay it to the corresponding service via care operations message server 340, as well as to connections gateway 360 or database gateway 370 if appropriate, for execution. At operation 2205, if the caregiver user is not done tracking patients, process 2200 loops back to operation 2202 and repeats as often or as long as needed. Otherwise, in operation 2206 the caregiver user may log off from portal 332, finishing process 2200 at operation 2207.

FIG. 23 provides detail of family member track patient process 2300, whereby a family member may monitor or communicate with the related patient. Process 2300 begins with operation 2301, in which a family member user may log on using the family member portal web service 334. The logged-on family member may then in operation 2302 select a patient from a list of those to whom the family member is related, and view the patient information and available commands subsequently presented by portal 334.

Depending on the facility's family member policy and corresponding permissions, as well as any additional constraints imposed by the patient or an assigned caregiver, the dashboard thus presented may provide a vast array of patient status information, including without limitation real-time sensor readings such as heart rate, temperature, blood pressure, location, and others; sensor reading history, including time-series graphs or tables; notifications sent or received regarding the patient and any related medicines, conditions, environment, or other matters; names and contact information for assigned caregivers; a view of the latest display content from the active patient sensor package 120, showing what the patient sees; and status of ongoing command execution. Similarly, and again depending on the facility's family member policy, corresponding permissions, and additional patient or caregiver constraints, the dashboard may also provide buttons, menus, and other command forms providing the ability to initiate various actions, including without limitation initiating or terminating audio or video monitoring of the patient via the assigned patient sensor package 120; exchanging text messages with the patient or a logged-on caregiver; and initiating or terminating an audio-only or an audio and video connection to converse with the patient or a logged-on facility's family member policy and corresponding permissions.

Given this universe of options, in operation 2303 the family member may initiate a permitted action or command, and in operation 2304 the portal web service 334 may log the action in databases 350 and relay it to the corresponding service via care operations message server 340, as well as to connections gateway 360 or database gateway 370 if appropriate, for execution. At operation 2305, if the family member user is not done tracking patients, process 2300 loops back to operation 2302 and repeats as often or as long as needed. Otherwise, in operation 2306 the family member user may log off from portal 334, finishing process 2300 at operation 2307.

The processes of FIGS. 4-23 may be implemented in various different ways without departing from the scope of the disclosure. For instance, the operations may be performed in different orders than shown. As another example, some processes may include additional operations and/or omit various listed operations.

In addition, while the examples shown may illustrate many individual modules as separate elements, one of ordinary skill in the art would recognize that these modules may be combined into a single functional block or element. One of ordinary skill in the art would also recognize that a single module may be divided into multiple modules.

IV. Computer System

Many of the processes and modules described above may be implemented as software processes that are specified as one or more sets of instructions recorded on a non-transitory storage medium. When these instructions are executed by one or more computational element(s) (e.g., microprocessors, microcontrollers, digital signal processors (DSPs), application-specific integrated circuits (ASICs), field programmable gate arrays (FPGAs), etc.) the instructions cause the computational element(s) to perform actions specified in the instructions.

In some embodiments, various processes and modules described above may be implemented completely using electronic circuitry that may include various sets of devices or elements (e.g., sensors, logic gates, analog to digital converters, digital to analog converters, comparators, etc.). Such circuitry may be able to perform functions and/or features that may be associated with various software elements described throughout.

Figure 24:
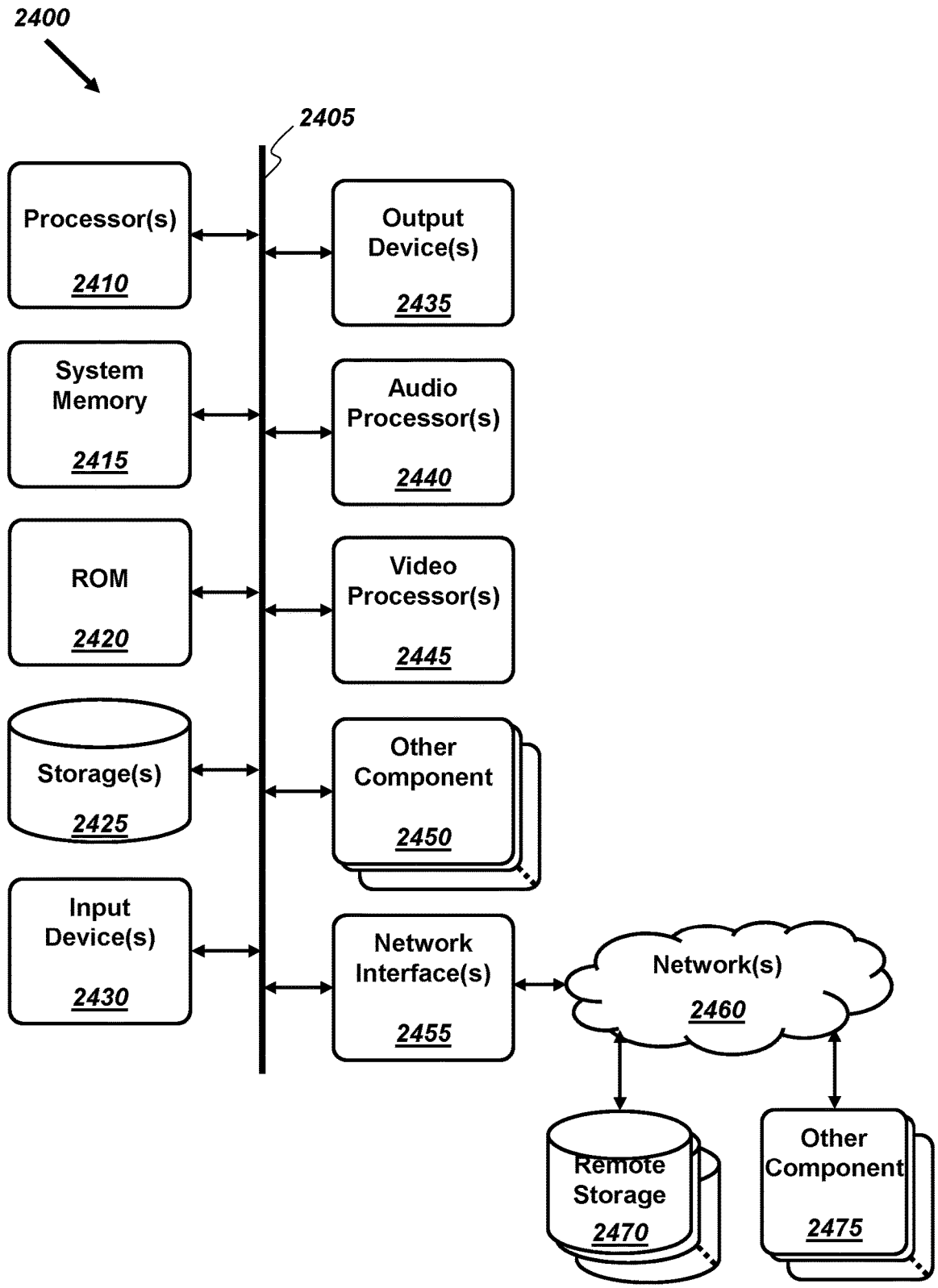
FIG. 24 illustrates a schematic block diagram of an exemplary computer system 2400 used to implement some embodiments.

FIG. 24 illustrates a schematic block diagram of an exemplary computer system 2400 used to implement some embodiments. For example, the system described above in reference to FIG. 1 may be at least partially implemented using instances of computer system 2400, particularly cloud platform 102, appliance platform 103, and the various workstations 110, 111, and 115. As another example, the processes described in reference to FIGS. 4-23 may be at least partially implemented using sets of instructions that are executed using computer system 2400. Further, the hardware aspects of patient sensor package 120 in FIG. 2 may be a specialized example of computer system 2400—particularly the processor and memory portions of processor, memory, and operating system 201; the interface hardware portions of the various interface hardware and drivers 202, 203, 204, and 205; and the variety of peripherals including communication ports and radios 221, 222, 223, 224, and 225, power circuits 231 and 232, and sensors and actuators 241, 242, 243, 244, 245, 251, 252, 253, 254, and 255.

Computer system 2400 may be implemented using various appropriate devices. For instance, the computer system may be implemented using one or more personal computers (PCs), servers, mobile devices (e.g., a smartphone or smartwatch), tablet devices, and/or any other appropriate devices. The various devices may work alone (e.g., the computer system may be implemented as a single PC) or in conjunction (e.g., some components of the computer system may be provided by a mobile device while other components are provided by a tablet device).

As shown, computer system 2400 may include at least one communication bus 2405, one or more processors 2410, a system memory 2415, a read-only memory (ROM) 2420, permanent storage devices 2425, input devices 2430, output devices 2435, audio processors 2440, video processors 2445, various other components 2450, and one or more network interfaces 2455.

Bus 2405 represents all communication pathways among the elements of computer system 2400. Such pathways may include wired, wireless, optical, and/or other appropriate communication pathways. For example, input devices 2430 and/or output devices 2435 may be coupled to the system 2400 using a wireless connection protocol or system.

The processor 2410 may, in order to execute the processes of some embodiments, retrieve instructions to execute and/or data to process from components such as system memory 2415, ROM 2420, and permanent storage device 2425. Such instructions and data may be passed over bus 2405.

System memory 2415 may be a volatile read-and-write memory, such as a random access memory (RAM). The system memory may store some of the instructions and data that the processor uses at runtime. The sets of instructions and/or data used to implement some embodiments may be stored in the system memory 2415, the permanent storage device 2425, and/or the read-only memory 2420. ROM 2420 may store static data and instructions that may be used by processor 2410 and/or other elements of the computer system.

Permanent storage device 2425 may be a read-and-write memory device. The permanent storage device may be a non-volatile memory unit that stores instructions and data even when computer system 2400 is off or unpowered. Computer system 2400 may use a removable storage device and/or a remote storage device as the permanent storage device.

Input devices 2430 may enable a user to communicate information to the computer system and/or manipulate various operations of the system. The input devices may include keyboards, cursor control devices, audio input devices and/or video input devices. Output devices 2435 may include printers, displays, audio devices, etc. Some or all of the input and/or output devices may be wirelessly or optically connected to the computer system 2400.

Audio processor 2440 may process and/or generate audio data and/or instructions. The audio processor may be able to receive audio data from an input device 2430 such as a microphone. The audio processor 2440 may be able to provide audio data to output devices 2440 such as a set of speakers. The audio data may include digital information and/or analog signals. The audio processor 2440 may be able to analyze and/or otherwise evaluate audio data (e.g., by determining qualities such as signal to noise ratio, dynamic range, etc.). In addition, the audio processor may perform various audio processing functions (e.g., equalization, compression, etc.).

The video processor 2445 (or graphics processing unit) may process and/or generate video data and/or instructions. The video processor may be able to receive video data from an input device 2430 such as a camera. The video processor 2445 may be able to provide video data to an output device 2440 such as a display. The video data may include digital information and/or analog signals. The video processor 2445 may be able to analyze and/or otherwise evaluate video data (e.g., by determining qualities such as resolution, frame rate, etc.). In addition, the video processor may perform various video processing functions (e.g., contrast adjustment or normalization, color adjustment, etc.). Furthermore, the video processor may be able to render graphic elements and/or video.

Other components 2450 may perform various other functions including providing storage, interfacing with external systems or components, etc.

Finally, as shown in FIG. 24, computer system 2400 may include one or more network interfaces 2455 that are able to connect to one or more networks 2460. For example, computer system 2400 may be coupled to a web server on the Internet such that a web browser executing on computer system 2400 may interact with the web server as a user interacts with an interface that operates in the web browser. Computer system 2400 may be able to access one or more remote storages 2470 and one or more external components 2475 through the network interface 2455 and network 2460. The network interface(s) 2455 may include one or more application programming interfaces (APIs) that may allow the computer system 2400 to access remote systems and/or storages and also may allow remote systems and/or storages to access computer system 2400 (or elements thereof).

As used in this specification and any claims of this application, the terms "computer", "server", "processor", and "memory" all refer to electronic devices. These terms exclude people or groups of people. As used in this specification and any claims of this application, the term "non-transitory storage medium" is entirely restricted to tangible, physical objects that store information in a form that is readable by electronic devices. These terms exclude any wireless or other ephemeral signals.

It should be recognized by one of ordinary skill in the art that any or all of the components of computer system 2400 may be used in conjunction with some embodiments. Moreover, one of ordinary skill in the art will appreciate that many other system configurations may also be used in conjunction with some embodiments or components of some embodiments.

In addition, while the examples shown may illustrate many individual modules as separate elements, one of ordinary skill in the art would recognize that these modules may be combined into a single functional block or element. One of ordinary skill in the art would also recognize that a single module may be divided into multiple modules.

The foregoing relates to illustrative details of exemplary embodiments of the invention and modifications may be made without departing from the scope of the invention as defined by the following claims.

What is claimed is:

1. A method comprising:
   assigning a first caregiver to a patient upon the patient being admitted to a first care facility;
   assigning a patient sensor package to the patient, wherein the patient sensor package is configured to connect to a first care operations service suite associated with the first care facility via a first network;
   automatically configuring the patient sensor package to send patient data to the first care operations service suite based on a set of care facility policies associated with the first care facility, and according to caregiver settings associated with the first caregiver;
   receiving patient data from the patient sensor package via the first network and storing the patient data in a database associated with the first care operations service suite;
   determining that the patient has transferred from the first care facility to a second care facility;
   automatically reconfiguring the patient sensor package to connect via a second network to a second care operations service suite associated with the second care facility;
   automatically assigning a second caregiver associated with the second care facility to the patient;
   automatically configuring the patient sensor package to send the patient data to the second care operations service suite based on a set of care facility policies associated with the second care facility, and according to caregiver settings associated with the second caregiver; and
   presenting sensor data to at least one of a first remote computing device associated with the first caregiver or a second remote computing device associate with the second caregiver.

2. The method of claim 1, further comprising:
   discharging the patient from the second care facility and disabling the patient sensor package.

3. The method of claim 1, further comprising:
   facilitating audio, audio/visual, and text communication between a remote computing device associated with the patient and the second remote computing device associated with the second caregiver.

4. The method of claim 1, further comprising:
   sending the patient data to a remote computing device associated with a family member user authorized by the patient to participate in the patient's care; and
   facilitating audio, audio/visual, and text communication between the remote computing device associated with the family member user and the second caregiver.

5. The method of claim 1, wherein the first remote computing device comprises an administrator workstation, and wherein the administrator workstation is configured to access an operations service suite for allowing an administrator user to enroll, admit, transfer, or discharge the patient via a care operations service suite.

6. The method of claim 1, wherein the first remote computing device comprises a personal computing device accessed by a family member user, and wherein the personal computing device is configured to access a care operations service suite for allowing the family member user to track patient information, monitor the patient via the patient sensor package, and communicate with the second remote computing device associated with the second caregiver.

7. A patient monitoring system comprising:
   a patient sensor package configured to track patient information; and
   a computing element for executing a care operations service suite, wherein the care operations service suite is configured to:
     assign a first caregiver to a patient upon the patient being admitted to a first care facility;
     assign a patient sensor package to the patient, wherein the patient sensor package is configured to connect to a first care operations service suite associated with the first care facility via a first network;
     automatically configure the patient sensor package to send patient data to the first care operations service suite based on a set of care facility policies associated with the first care facility, and according to caregiver settings associated with the first caregiver;
     receive patient data from the patient sensor package via the first network and storing the patient data in a database associated with the first care operations service suite;
     determine that the patient has transferred from the first care facility to a second care facility;
     automatically reconfigure the patient sensor package to connect via a second network to a second care operations service suite associated with the second care facility;
     automatically assign a second caregiver associated with the second care facility to the patient;
     automatically configure the patient sensor package to send the patient data to the second care operations service suite based on a set of care facility policies associated with the second care facility, and according to caregiver settings associated with the second caregiver; and
     present sensor data to at least one of a first remote computing device associated with the first caregiver or a second remote computing device associate with the second caregiver.

8. The patient monitoring system of claim 7, wherein the second remote computing device comprises an administrator workstation or a caregiver workstation.

9. The patient monitoring system of claim 8, wherein the administrator workstation is configured to access an operations service suite for allowing an administrator user to enroll, admit, transfer, or discharge the patient via the care operations service suite.

10. The patient monitoring system of claim 8, wherein the caregiver workstation is configured to access the care operations service suite for allowing a caregiver to track patient information, monitor the patient via the patient sensor package, and communicate with the patient via the patient sensor package.

11. The patient monitoring system of claim 7, wherein the first remote computing device comprises a personal computing device accessed by a family member user.

12. The patient monitoring system of claim 11, wherein the personal computing device is configured to access the care operations service suite for allowing the family member user to track patient information, monitor the patient via the patient sensor package, and communicate with the second remote computing device associated with the second caregiver.

13. The patient monitoring system of claim 7, wherein the patient sensor package comprises:

an embedded computer with memory and processing capability;

a number of sensors measuring body functions and indicators relevant to health;

a number of communication interfaces with both wired and wireless connectivity;

a number of user interfaces with audio/visual and haptic connectivity; and an application suite supporting automatic collection of sensor information by the care operations service suite.

14. The patient monitoring system of claim 13, wherein the application suite further supports audio, audio/visual, and text communication between the patient and a caregiver.

15. The patient monitoring system of claim 13, wherein the patient sensor package is disposed in a wristwatch, chestband, headband, choker, necklace, sash, vest, hat, belt, armband, sock, glove, or pendant.

16. The patient monitoring system of claim 7, wherein the care operations service suite comprises:

a care operations message server interacting with patient sensor packages and configured to provide message services corresponding to the patient sensor packages, wherein the messaging services provides information related to a configuration, connection, location, sensor, or presentation manager for the patient sensor packages;

a care operations web server interacting with users and configured to provide portal web services to administrator, caregiver, patient, or family member users; and a management server interacting with system managers and configured to provide log, data backup, software update, file transfer, command-line, or graphical control management services.

17. The patient monitoring system of claim 16, wherein the care operations service suite further comprises a communications gateway or an external information database gateway.

18. The patient monitoring system of claim 16, wherein the care operations service suite further comprises an autonomous data analysis and application support platform that provides notification and action initiation, diagnostic event correlation, and diagnostic trend detection capabilities.

19. The patient monitoring system of claim 16, wherein the computing element for executing the care operations service suite comprises shared computing elements in a virtual private cloud provided by a HIPAA-compliant public cloud service, and accessed via the Internet.

20. The patient monitoring system of claim 16, wherein the computing element for executing the care operations service suite comprises dedicated computing elements located in a care facility and is accessed via a local area network associated with the care facility.

21. The patient monitoring system of claim 16, wherein the computing element for executing the care operations service suite comprises shared computing elements in a private cloud located in a corporate data center and is accessed via a virtual private network.

* * * * *